(12) United States Patent
Maclachlan

(10) Patent No.: US 6,284,736 B1
(45) Date of Patent: Sep. 4, 2001

(54) AMPHOTERICIN DERIVATIVES

(75) Inventor: William Skinner Maclachlan, Epsom (GB)

(73) Assignee: Beecham Group, plc, Middlesex (GB)

( * ) Notice: Subject to any disclaimer, the term of this patent is extended or adjusted under 35 U.S.C. 154(b) by 0 days.

(21) Appl. No.: 07/626,197

(22) Filed: Dec. 6, 1990

(30) Foreign Application Priority Data

Dec. 8, 1989 (GB) .................................. 8927859
Jun. 18, 1990 (GB) .................................. 9013546

(51) Int. Cl.[7] .............................. A61K 31/70; C07H 17/08
(52) U.S. Cl. ........................................... 514/31; 536/6.5
(58) Field of Search ..................... 536/6.5, 7.1; 514/31

(56) References Cited

U.S. PATENT DOCUMENTS

| | | | | |
|---|---|---|---|---|
| 3,361,737 | * | 1/1968 | Jones ....................... | 536/7.1 |
| 3,945,993 | * | 3/1976 | Schaffner et al. ........... | 536/6.5 |
| 4,365,058 | * | 12/1982 | Falkowski et al. ........... | 536/6.5 |

FOREIGN PATENT DOCUMENTS

| 2173632 | 2/1971 | (FR) | ....................... 536/6.5 |
|---|---|---|---|

OTHER PUBLICATIONS

W. Szponarski et al. "Interaction of 14C–labelled amphotericin B derivatives with human erythrocytes: relationship between binding and induced K + leak". (1988) Biochimica et Biophysica Acta 938, 97–106.

* cited by examiner

Primary Examiner—Elli Peselev
(74) Attorney, Agent, or Firm—Hopgood, Calimafde Kalil & Judlowe

(57) ABSTRACT

A compound of formula (I), or a pharmaceutically acceptable salt thereof:

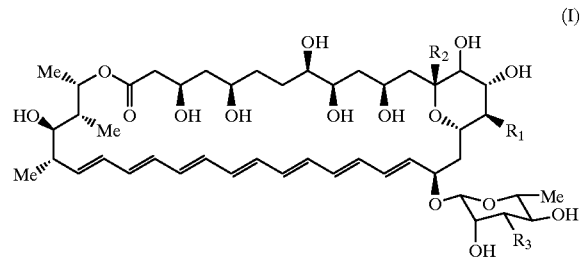

wherein $R_1$ is a carboxylic acid group, a derivative thereof, a ketone residue, an aldehyde function or optionally substituted methyl; $R_2$ is hydroxy, $C_{1-8}$ alkoxy or a fluorine atom; and $R_3$ is an amino group or a derivative thereof.

11 Claims, No Drawings

AMPHOTERICIN DERIVATIVES

The present invention relates to novel compounds having pharmacological activity, their preparation, compositions containing them and their use in the treatment of fungal infections in animals, including humans.

The polyene macrolide amphotericin B, produced by *Streptomyces nodosus*, is widely used for the treatment of fungal infections.

Amphotericin B is the only complex polyene macrolide whose molecular structure and absolute configuration has been firmly established by X-ray crystallographic analysis. Amphotericin B has the formula (A):

(A)

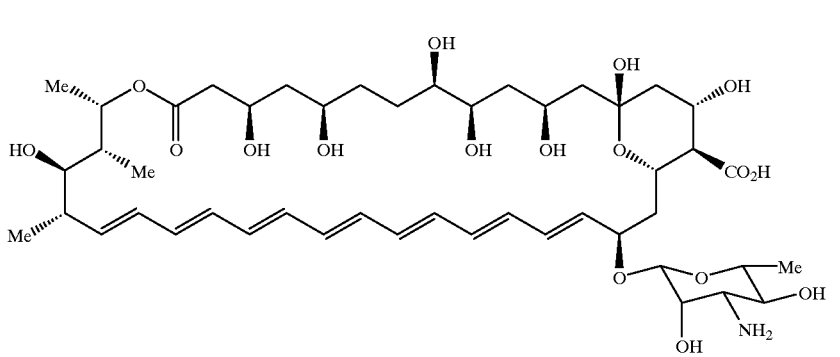

Derivatives of amphotericin B substituted at the 14-position of the amphotericin B nucleus have now been prepared. These derivatives have been found to have antifungal activity and have potential utility as anti-fungal agents.

Accordingly, the present invention provides a compound of formula (I), or a pharmaceutically acceptable salt thereof:

(I)

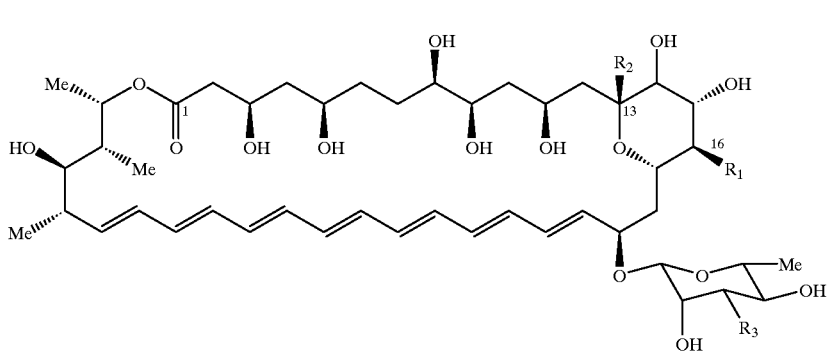

wherein $R_1$ is a carboxylic acid group, a derivative thereof, a ketone residue, an aldehyde function or optionally substituted methyl; $R_2$ is hydroxy, $C_{1-8}$ alkoxy or a fluorine atom; and $R_3$ is an amino group or a derivative thereof.

As used herein, the term carboxylic acid group derivative includes esters, and amides. Ester groups include alkoxycarbonyl, alkenyloxycarbonyl, aryloxycarbonyl, heteroaryloxycarbonyl, aralkyloxycarbonyl and heteroaralkyloxycarbonyl goups. Amides include primary, secondary and tertiary amides. For example the amino moiety may be substituted by one or two alkyl groups. A ketone residue may be an alkyl, aryl or heteroaryl ketone residue. A suitable value for $R_1$ when optionally substituted methyl is hydroxymethyl.

Unless otherwise specified, each alkyl, alkenyl or alkoxy group is preferably a $C_{1-6}$ group, more preferably a $C_{1-4}$ group and may be straight chain or branched.

When used herein, the term aryl includes both monocyclic and bicyclic carbocyclic moieties, for example phenyl and naphthyl. An aryl moiety may be mono-, di-, or tri-substituted by groups including carboxy, alkoxycarbonyl, hydroxy, alkyl, alkoxy, halogen, and amino optionally substituted by alkyl, and is preferably mono- or di-substituted.

The term heteroaryl includes 5- or 6-membered monocyclic and 9- or 10-membered bicyclic heteroaryl.

In addition, 5- or 6-membered monocyclic and 9- or 10-membered bicyclic heteroaryl preferably contain one or two heteroatoms selected from nitrogen, oxygen and sulphur which in the case of there being more than one heteroatom may be the same or different. When 9- or 10-membered bicyclic heteroaryl, the two rings are fused, preferably with one 5- or 6-membered ring containing a single heteroatom.

Unless otherwise specified, the term halogen includes fluorine, chlorine, bromine and iodine.

When used herein, the term amino group derivative includes acyl derivatives, in particular acyl derivatives bearing a basic substituent such as N-D-lysyl and N-D-ornithyl derivatives, guanidine derivatives, and N-glycosyl derivatives. The preparation of suitable amino group derivatives is described in European Patent Publication 0 010 297 (Schering), European Patent Publication 0 031 722 (Dumex) and U.S. Pat. No. 4,195,172.

Compounds of formula (I) and salts thereof may also form solvates such as hydrates and the invention also extends to these forms. When referred to herein it is understood that a compound of the invention or a salt thereof includes solvates.

Pharmaceutically acceptable salts of compounds of formula (I) may be formed conventionally, for example by reaction with the appropriate acid or base.

Compounds of formula (I) can form acid addition salts with acids, such as conventional pharmaceutically acceptable acids, for example hydrochloric, hydrobromic, phosphoric, acetic, fumaric, salicylic, citric, lactic, mandelic, tartaric, oxalic, methanesulphonic, aspartic and ascorbic. The invention also extends to quaternary salts.

Compounds of formula (I) wherein $R_1$ is hydroxycarbonyl can form basic addition salts with bases, such as conventional pharmaceutically acceptable bases, for example sodium hydrogen carbonate, potassium carbonate, lithium hydroxide, triethylamine, pyridine, lutidine and N-methylglucamine.

The formation of compounds of formula (I) of the present invention creates a further chiral centre at the 14-position of the amphotericin B nucleus. Compounds of formula (I) are therefore capable of existing in different stereoisomeric forms. The invention extends to each of these forms and to mixtures thereof. Compounds of formula (I) having different stereochemistry at the 14-position may be obtained by stereospecific syntheses, as hereinafter described.

Suitable values for $R_1$ include hydroxycarbonyl, $C_{1-4}$ alkoxycarbonyl such as methoxycarbonyl, $C_{1-4}$ alkenyloxycarbonyl such as prop-2-enyloxycarbonyl, and hydroxymethyl.

Suitable values for $R_2$ include hydroxy, $C_{1-4}$ alkoxy such as methoxy, and fluoro.

Preferably $R_3$ is an amino group.

The present invention also provides a process for the preparation of compounds of formula (I) which process comprises the reaction of a compound of formula (II):

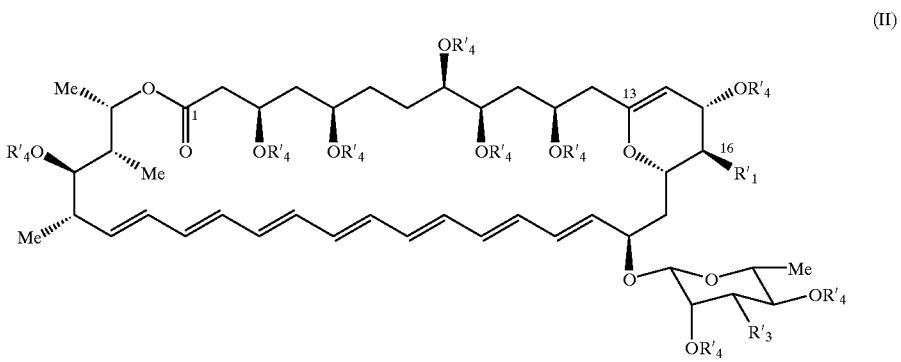

(II)

wherein $R_1'$ is $R_1$ as defined for formula (I); $R_3'$ is a protected amino group; and each $R_4'$ is hydrogen or a silyl protecting group; with a peracid, followed by selective substitution at the anomeric 13-position of the intermediate so formed in the presence of a compound $R_2$—H where $R_2$ is as defined for formula (I); and thereafter, optionally or as necessary and in any appropriate order converting $R_3'$ to an $R_3$ amino group, removing $R_4'$ when a silyl protecting group, interconverting $R_1$, interconverting $R_2$, forming an amino group derivative, and forming a pharmaceutically acceptable salt.

A suitable peracid for reaction with a compound of formula (II) is m-chloroperbenzoic acid. When $R_4'$ is silyl, the reaction is suitably carried out under anhydrous conditions at reduced temperature in an inert solvent, for example n-hexane, methylene chloride or tetrahydrofuran.

The intermediate formed by reaction with a peracid may be progressed, without isolation, to a compound of formula (I) by carrying out the reaction with peracid in the presence of a compound $R_2$—H (where $R_2$ is hydroxy or $C_{1-8}$ alkoxy). For example, where $R_2$ is hydroxy and $R_4'$ is hydrogen, the reaction with peracid is conveniently carried out in aqueous tetrahydroforan. Alternatively, the isolated intermediate may be further reacted with a compound $R_2$—H.

Where each $R_4'$ in a compound of formula (II) is a silyl protecting group, the intermediate formed by reaction with a peracid has been isolated and shown to be a compound of formula (III):

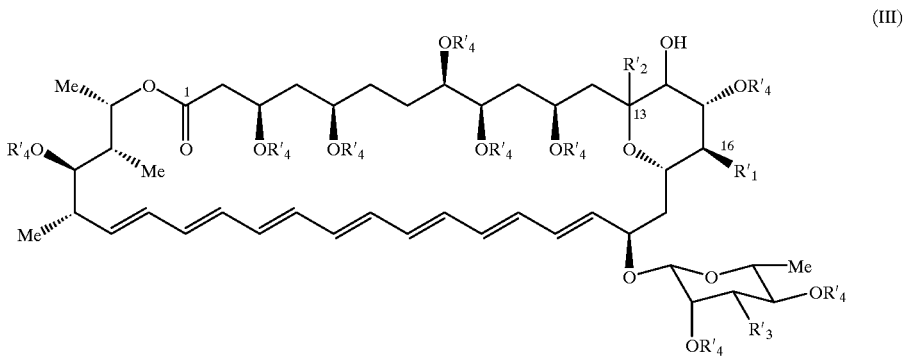

(III)

wherein $R_1'$ and $R_3'$ are as defined for formula (II); each $R_4'$ is a silyl protecting group; and $R_2'$ is acyloxy. It will be appreciated that the $R_2'$ acyloxy substituent at position-13 will correspond to the chosen peracid. Thus, for example, when the peracid is m-chloroperbenzoic acid, $R_2'$ is m-chlorobenzoyloxy.

The 14-hydroxy substituent in compounds of formula (III) has been shown by spectroscopic analysis to have the (S)-configuration. (S)-stereochemistry is retained at the 14-position in compounds of the invention of formula (I) when prepared by this process variant.

Conversely, compounds of formula (I) prepared from an intermediate of formula (II) in which each $R_4'$ is hydrogen have been shown to have (R)-stereochemistry at the 14-position.

Where an intermediate compound of formula (III) is isolated, the conditions under which selective substitution at the anomeric 13-position is effected may be varied according to the desired value of $R_2$.

Thus where $R_2$ in a compound of formula (I) is $C_{1-8}$ alkoxy, a compound of formula (III) may be dissolved in an inert solvent and stirred at ambient temperature with the corresponding $C_{1-8}$ alkyl alcohol. For example, where $R_2$ in a compound of formula (I) is methoxy, a compound of formula (III) may be stirred for 20 to 24 hours in a mixture of methylene chloride and methanol.

Where $R_2$ in a compound of formula (I) is hydroxy, a compound of formula (III) may be conveniently hydrolysed using ion-exchange chromatography using an acidic ion-exchange resin. The resin Amberlyst 15 is particulary suitable for ester substitution, for example using a solution of a compound of formula (III) in a solvent such as n-hexane.

Where $R_2$ in a compound of formula (I) is fluorine, a compound of formula (III) may be dissolved in an inert solvent, for example tetrahydrofuran, and treated with hydrogen fluoride-pyridine under anhydrous conditions. This procedure will result in the concomitant cleavage of the silyl protecting groups, $R_4'$.

Interconversion of $R_2$ to further values of $R_2$ may be carried out using standard methodology. Thus an $R_2$ fluorine atom may be converted to $R_2$ hydroxy under aqueous conditions in the presence of an acid catalyst such as pyridinium p-toluenesulphonate or 10-camphorsulphonic acid.

Suitable values for amine protection groups in $R_3'$ include
trifluoroacetyl, 9-fluorenylmethoxycarbonyl,
2,2,2-trichloroethoxycarbonyl,
2-phenylsulphonylethoxy-carbonyl and
2-trimethylsilylethoxycarbonyl. A preferred amine protection group is 9-fluorenylmethoxycarbonyl.

Conversion of a protected amino group $R_3'$ to $R_3$ amino may be carried out under basic conditions.

An amine protection group such as trifluoroacetyl may be removed using a base such as ammonia or potassium carbonate in anhydrous methanol.

An amine protection group, such as 9-fluorenylmethoxy carbonyl, may be removed under basic conditions in a solvent such as methanolic dimethyl sulphoxide. Suitable bases for amine deprotection include ammonia, dialkylamines such as dimethylamine and diethylamine, trialkylamines such as triethylamine, cyclic amines and especially cyclic secondary amines such as morpholine, piperazine and more especially piperidine, and diazabicyclic bases such as 1,5-diazabicyclo[4.3.0]non-5-ene (DBN) and preferably 1,8-diazabicyclo[5.4.0]undec-7-ene (DBU).

The amine deprotection may be carried out using from 1–10 equivalents of base, preferably from 1–2 equivalents, at reduced or elevated temperatures, for example from −30° C. to 50° C. and preferably from 0° C. to room temperature, over a time period ranging from 1 minute to 5 hours and preferably from 30 minutes to 2.5 hours.

Interconversion of $R_1$ to further values of $R_1$ may be carried out using functional group interconversion procedures suitable for use in the field of polyene macrolide chemistry.

For example, an $R_1$ carboxylic acid group may be esterified to give an $R_1$ methyl ester using diazomethane in an ether solvent at reduced temperatures. An allyl ester may be converted to a carboxylic acid group by treatment with an amine such as pyrrolidine or morpholine in the presence of a catalytic amount of a palladium (0) catalyst, for example tetrakis(triphenylphosphine) palladium (0).

It may be convenient or necessary to carry out $R_1$ functional group interconversions, if desired, using compounds of formula (I) in which $R_3$ is in protected form.

Suitable $R_4'$ silyl protecting groups include trimethylsilyl, triethylsilyl and t-butyldimethylsilyl, preferably trimethylsilyl or triethylsilyl. $R_4'$ silyl protecting groups may be removed using known deprotection methods, for example using a solution of hydrogen fluoride-pyridine as described above. Cleavage may be effected at normal or reduced temperature, for example from −10° C. to 50° C. and preferably from 0° C. to room temperature, over a time period of up to 60 hours and preferably from 4 to 24 hours.

Intermediate compounds of formula (II) may be prepared from the natural product amphotericin B by protecting the amine function of the 19-position sugar moiety with an amine protection group, derivatising the 16-position carboxy group as required, and treatment with a silylating agent. These transformations may be carried out in any appropriate order.

Amine protection groups may be introduced by standard procedures. For example, a trifluoroacetyl amine protection group may be introduced by reaction of the primary amine with ethyl trifluoroacetate in a base such as diisopropylethylamine in methanol-dimethyl sulphoxide or methanol-dimethylformamide solvent mixture at reduced to normal temperatures, for example at 0° C.

A 9-fluorenylmethoxycarbonyl group may be introduced by addition of N-(9-fluorenylmethoxycarbonyloxy)-succinimide to a slurry of the primary amine in methanol-dimethylformamide under anhydrous conditions in the presence of a base such as pyridine.

Alternatively, a 9-fluorenylmethoxycarbonyl amine protection group may be introduced by addition of 9-fluorenylmethyl chloroformate to a solution of the primary amine in methanol-dimethylformamide under anhydrous conditions, in the presence of a base such as potassium carbonate.

The 13-position anomeric hydroxyl group may optionally be selectively exchanged prior to reaction with a silylating agent by reaction with a $C_{1-8}$ alkyl alcohol as described above for the interconversion of $R_2$ hydroxy to $R_2$ alkoxy in compounds of formula (I).

Free hydroxyl groups may be silylated using standard procedures. The reaction with silyating agents such as trimethylsilyl trifluoromethanesulphonate and triethylsilyl trifluoromethanesulphonate may be carried out in a suitable inert solvent, for example dichloromethane, under an inert atmosphere over a range of temperatures, for example from 0° C. to 50° C. The reaction is conveniently effected using an excess of the silylating agent in the presence of a weak base, for example a pyridine derivative such as 2,6-lutidine. Alternatively, when a liquid, the base may replace the solvent. The reaction time is dependent on the size of the silyl group, ranging from a few minutes for a trimethylsilyl group to several hours for larger silyl groups.

The introduction of $R_4$' silyl protecting groups is accompanied by elimination or partial elimination of the 13-position substituent to give 13,14-anhydroamphotericin B derivatives. The extent of the elimination varies according to both the silylating agent and the solvent, it being dominant when the solvent is dichloromethane and the silylating agent is trimethylsilyl triflate. Where the silylation reaction results in a mixture of compounds, these may be separated by chromatographic techniques.

After formation of the 13,14-anhydro intermediate of formula (II) in which each $R_4$' is a silyl protecting group, it will be necessary to remove the $R_4$' silyl protecting groups in order to carry out the reaction with peracid to prepare a compound of formula (I) with (R)-stereochemistry at the 14-position. $R_4$' silylation groups may be removed as hereinbefore described.

Intermediate compounds of formula (II) may be prepared using procedures described in European Patent Publication, EP-A 0 350 164 (Beecham).

Intermediate compounds of formula (III) are novel and as such form part of the invention.

The compounds of the formula (I) and their pharmaceutically acceptable salts are anti-fungal agents, potentially useful in combating fungal infections in animals, including humans. For example they are potentially useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus*, Coccidioides, Paracoccidioides, Histoplasma or Blastomyces spp. They may also be of use in treating eumycotic mycetoma, chromoblastomycosis, and phycomycosis.

The invention further provides a pharmaceutical composition comprising a compound of the formula (I) or a pharmaceutically acceptable salt thereof, together with a pharmaceutically acceptable diluent or carrier. The composition is preferably for human use in tablet, capsule, injectable or cream form.

The invention also provides for the preparation of a pharmaceutical composition which comprises admixing a compound of formula (I), or a pharmaceutically acceptable salt thereof and a pharmaceutically acceptable carrier.

For human use, an antifungal compound of the formula (I) or a pharmaceutically acceptable salt thereof can be administered alone, but will generally be administered in admixture with a pharmaceutical carrier selected with regard to the intended route of administration and standard pharmaceutical practice. For example, it may be administered orally in the form of a tablet containing such excipients as starch or lactose, or in a capsule or ovule either alone or in admixture with excipients, or in the form of an elixir or suspension containing a flavouring or colouring agent. A compound may be injected parenterally, for example, intravenously, intramuscularly or subcutaneously. For parenteral administration, a compound is best used in the form of a sterile aqueous solution which may contain other substances, for example, enough salts or glucose to make the solution isotonic.

For oral and parenteral administration to human patients, it is expected that the daily dosage level of an antifungal compound of the formula (I) will be from 0.1 to 1 mg/kg (in divided doses) when administered by either the oral or parenteral route. Thus tablets or capsules can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

Alternatively, an antifungal compound of formula (I) can be administered in the form of a suppository or pessary, or it may be applied topically in the form of a lotion, solution, cream, ointment or dusting powder. For example, a compound can be incorporated into a cream consisting of an aqueous emulsion of polyethylene glycols or liquid paraffin; or can be incorporated, at a concentration between 1 and 10%, into an ointment consisting of a white wax or white soft paraffin base together with such stabilizers and preservatives as may be required.

Within the indicated dose range, no adverse toxicological effects have been observed with the compounds of the invention which would preclude their administration to suitable patients for the treatment of fungal infections.

The present invention provides a compound of formula (I) or a pharmaceutically acceptable salt thereof for use as an active therapeutic substance.

A compound for use as an active therapeutic substance is intended for use in the treatment of disorders in animals including humans. As stated above, compounds of formula (I) and their pharmaceutically acceptable salts have anti-fungal activity and are potentially useful in combating fungal infections in animals, including humans.

Accordingly the present invention further provides a compound of formula (I) or a pharmaceutically acceptable salt thereof for use in the treatment of fungal infections.

The present invention additionally provides a method of treatment of fungal infections in animals, including humans, which comprises administering an effective anti-fungal amount of a compound of formula (I) or a pharmaceutically acceptable salt thereof to the animal.

The present invention also provides the use of a compound of formula (I) or a pharmaceutically acceptable salt thereof for the manufacture of a medicament for use in the treatment of fungal infections in animals, including humans.

The following Descriptions and Examples illustrate the preparation of compounds of formula (I). The abbreviations 'TMS', 'TES' and 'Fmoc' are used to represent trimethylsilyl, triethylsilyl and 9-fluorenylmethoxycarbonyl groups respectively.

DESCRIPTION 1

N-(9-Fluorenylmethoxycarbonyl)amphotericin B
(D1)

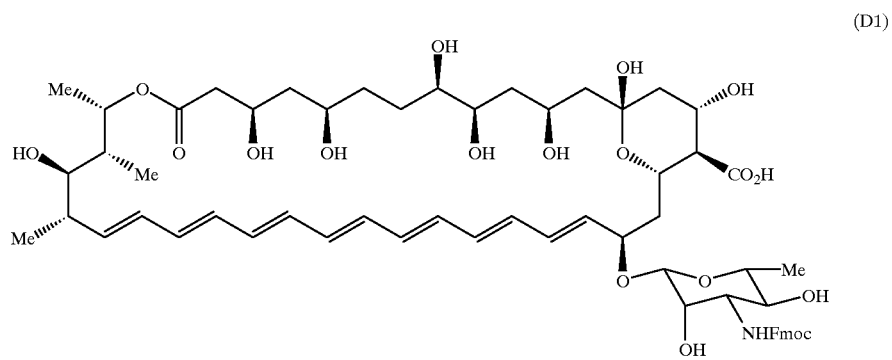

(D1)

Method A

To a solution of amphotericin B (5.0 g, 5.4 mmol) in dry dimethylsulphoxide (50 ml) and dry methanol (15 ml) was added dry pyridine(0.53 ml, 6.5 mmol). Under a nitrogen atmosphere was added solid N-(9-fluorenylmethoxycarbonyloxy)succinimide (2.59 g, 7.6 mmol). After stirring for 1 hr a further portion of N-(9-fluorenylmethoxycarbonyloxy)succinimide (0.28 g 0.8 mmol) was added. After a further 0.25 hrs glacial acetic acid (0.5 ml, 8.7 mmol) was added, the solution was diluted with methanol (35 ml) and poured into diethyl ether (5L). The precipitate was filtered, washed with diethyl ether and dried to give the title compound (D1) which was used without further purification.

Method B

To a solution of amphotericin B (0.50 g, 0.54 mmol) and anhydrous potassium carbonate (0.17 g, 1.2 mmol) in dry dimethylsulphoxide (10 ml) and dry methanol (2 ml) under a nitrogen atmosphere at 0° C., was added solid 9-fluorenylmethyl chloroformate (0.21 g, 0.81 mmol). After stirring for 1 hour a further portion of 9-fluorenylmethyl chloroformate (0.04 g, 0.17 mmol) was added. After 0.25 hours the reaction mixture was poured into distilled water (200 ml). The precipitate was collected by centrifugation, dissolved in methanol and evaporated in vacuo. The residue was dissolved in the minimum volume of a mixture of tetrahydrofuran and methanol (1:1) and poured into distilled water (200 ml, adjusted to pH 3.2 by the addition of glacial acetic acid). The preciptate was centrifuged, washed with water and dried in vacuo to give the title compound (D1) which was used without further purification.

DESCRIPTION 2

N-(9-Fluorenylmethoxycarbonyl)amphotericin B methyl ester (D2)

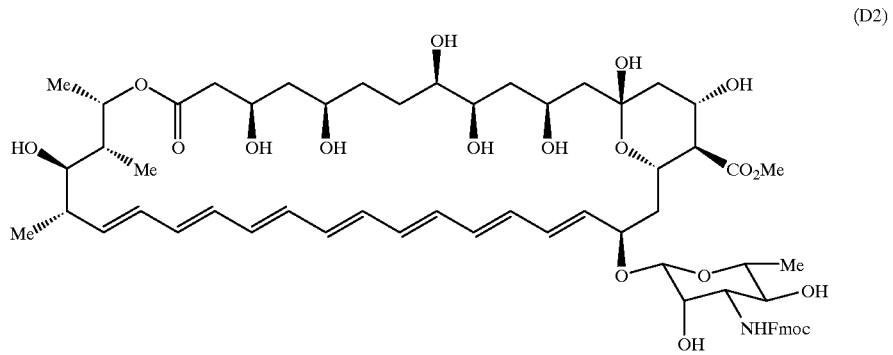

(D2)

Crude N-(9-fluorenylmethoxycarbonyl)amphotericin B (D1) (0.36 g, 0.31 mmol) was dissolved in 1:1 dimethyl-sulphoxide and methanol (20 ml). At 0° C. and with stirring, a solution of diazomethane in diethyl ether (25 ml) was added over 0.3 hours. The diazomethane was generated from Diazald[R] (0.39 g, 1.8 mmol); potassium hydroxide (0.18 g, 3.2 mmol); water (1 ml) and 2-(2-ethoxyethoxy)ethanol (2 ml). The reaction was stirred for a further 1.5 hours and then quenched cautiously with glacial acetic acid. The product was precipitated by pouring into diethyl ether. It was collected by centrifugation, washed with diethyl ether, dissolved in methanol and evaporated in vacuo.

The crude material was purified by means of medium pressure column chromatography on silica-gel eluting with ethyl acetate/methanol mixtures. The title compound (D2) was obtained as a yellow solid.

$\delta H$ (270 MHz) ($d_8$THF/$d_4$-MeOH) 7.78 (2H,d,J 6.9 Hz), 7.70 (2H,d,J 7.4 Hz), 7.35 (2H,dd,J 7.4 and 6.3 Hz), 7.28 (2H,t, 7.4 Hz), 6.63–5.93 (13H, complex), 5.50 (1H,m), 5.32 (1H,dd,J 10.2 and 14.8 Hz), 4.75–4.04 (10H, complex), 3.90–3.00 (8H, complex), 3.74 (3H,s), 2.50–1.15 (19H, complex), 1.28 (3H,d,J 6.2 Hz), 1.20 (3H,d,J 6.3 Hz), 1.10 (3H,d,J 6.3 Hz) and 0.99 (3H,d,J 7.2 Hz)ppm.

DESCRIPTION 3

N-(9-Fluorenylmethoxycarbonyl)-13-O-methylamphotericin B (D3)

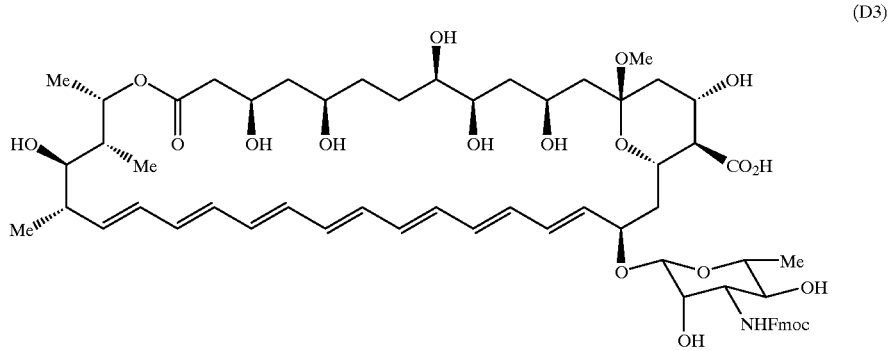

(D3)

N-(9-Fluorenylmethoxycarbonyl)amphotericin B (D1) (1.85 g, 1.61 mmol) and d-10-camphorsulphonic acid (156 mg, 0.67 mmol) were stirred in dry tetrahydrofuran (10 ml)/methanol (60 ml) at room temperature under nitrogen. After 15 minutes, triethylamine (0.14 ml, 102 mg, 1.01 mmol) was added, the mixture was filtered, concentrated to ca. 10 ml and poured into diethylether/n-hexane (800 ml 1:1). The precipitated product was collected by centrifugation, washed with diethylether/ethylacetate (1:1) and dried to give the title compound (D3) as a yellow powder.

HPLC: Reverse phase ODS 5$\mu$250×4.6 mm column; eluent 80% methanol-20% pH 3 phosphate buffer—1 ml.min$^{-1}$; detection wavelength 350 nm; retention time: 7.6 minutes.

DESCRIPTION 4

N-(9-Fluorenylmethoxycarbonyl)-3,5,8,9,11,15,35,
2',4'-nona-O-triethylsilyl-13,14-
anhydroamphotericin B (D4)

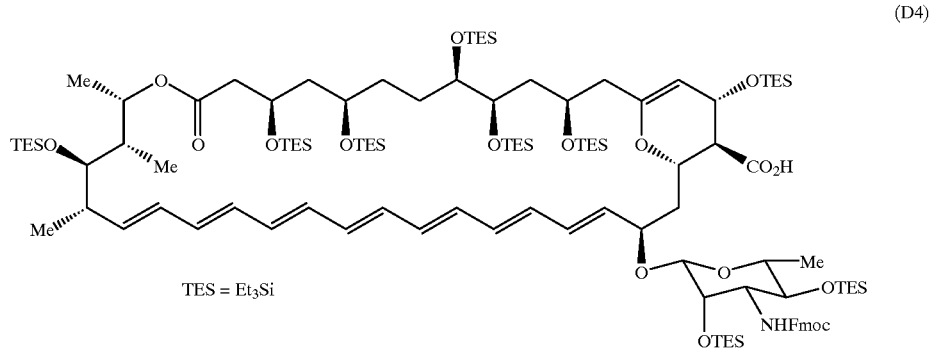

(D4)

TES = Et₃Si

The product of Description 3 (1.52 g) was suspended in dry dichloromethane (60 ml) at 0° C. under nitrogen and 2,6-lutidine (2.55 g, 2.76 ml, 23.80 mmol) followed by triethylsilyl trifluoromethanesulphonate (4.89 g, 4.18 ml, 18.50 mmol) were added via syringe. After stirring at 0° C. for 30 minutes the solvent was evaporated and the residue was dissolved in n-hexane, filtered and the filtrate was reconcentrated to give a brown oil. Purification by column chromatography on silica gel eluting with n-hexane/ethyl acetate mixtures gave the title product (D4).

The fractions containing the 13,14-anhydro product were washed with ice/0.2M sodium hydrogen sulphate solution to remove lutidine, dried over anhydrous magnesium sulphate, filtered and evaporated. Rf 0.40 (silica)-25% ethyl acetate in n-hexane. δH (400 MHz) ((CD₃)₂CO): 7.88(2H, d, J 7.5 Hz), 7.70(2H, d, J 7.5 Hz), 7.43(2H, t, J 7.4 Hz), 7.34(2H, t, J 7.4 Hz), 6.56–6.11 (12H, series of m), 5.99(1H, dd, J 6.0, 15.4 Hz), 5.55(1H, dd, J 9.4, 14.9 Hz), 5.34(1H, d, J 9.9 Hz), 4.80(1H, d, J 8.7 Hz), 4.73–4.60(2H, m), 4.63(1H, s), 4.59(1H, s), 4.50(1H, dd, J 6.5, 10.4 Hz), 4.35(1H, dd, J 6.5, 10.4 Hz), 4.32–4.17(3H, m), 4.12(1H, m), 4.01(1H, m), 3.90(1H, d, J 2.7 Hz) 3.85(1H, dd, J 2.8, 8.7 Hz), 3.80–3.66 (2H, m), 3.61(1H, dt, J 2.7, 9.7 Hz), 3.45(1H, t, J 9.1 Hz), 3.34(1H, m), 2.64(1H, dd, J 8.7, 10.8 Hz), 2.61–2.50(2H, m), 2.43(1H, m), 2.40–2.28(1H, m), 2.24–2.15(1H, m), 2.08–1.88(5H, series of m), 1.83–1.47(6H, series of m), 1.25(3H, d, J 6.1 Hz), 1.18(3H, d, J 6.0 Hz), 1.10–0.88(87H, series of m), 0.77–0.56(54H, series of m)ppm. The carboxylic acid proton was not observed. IR $\nu_{max}$ (thin film): 3445, 3500–2500 (broad, weak), 1737 (shoulder at 1720), 1680, 1510, 1461, 1416, 1380, 1310, 1240, 1192, 1169, 1080, 1007, 977, 740, 672cm⁻¹. Mass spectrum: FAB (3-NOBA matrix) Observed mass MH⁺ 2155.5. Calculated for $C_{116}H_{207}NO_{18}Si_9H^+$, 2155.

DESCRIPTION 5

N-(9-Fluorenylmethoxycarbonyl)-3,5,8,9,11,15,35,
2',-4'-nona-O-triethylsilyl-13,14-
anhydroamphotericin B methyl ester (D5)

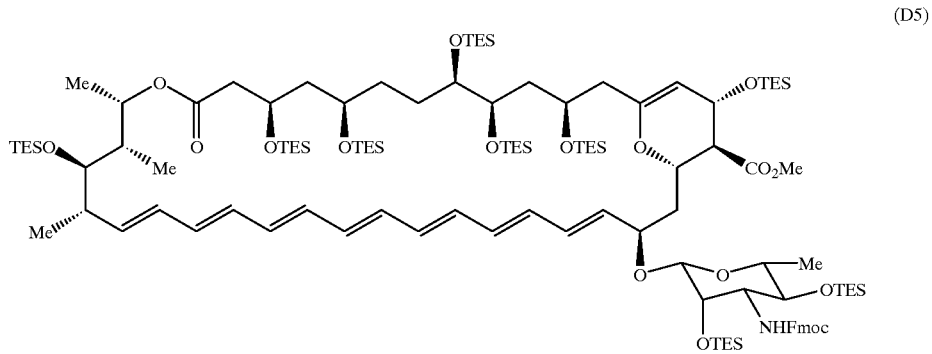

(D5)

Method A

N-(9-Fluorenylmethoxycarbonyl)amphotericin B methyl ester (D2) (1.6 g, 1.4mmol) was slurried in dry methylene chloride (12 ml). Under nitrogen, 2,6-lutidine (2.9 ml, 25.0 mmol) was added followed by trimethylsilyl trifluoromethanesulphonate (3.5 ml, 18.1 mmol). Some boiling of the solvent occurred. After 20 minutes the volatiles were evaporated in vacuo and the residue taken up in n-hexane (800 ml). The precipitate was removed by filtration and the filtrate evaporated.

The unpurified trimethylsilylated residue was dissolved in dry tetrahydrofuran (10 ml) in a plastic bottle. Under nitrogen, hydrogen fluoride.pyridine solution (56 ml of a solution made from 14.3 g of 70% hydrogen fluoride.pyridine reagent and 90 ml of pyridine made up to 250 ml with tetrahydrofuran—equivalent to 2M HF—112 mmol) was added via a plastic syringe. After stirring for four hours the reaction was poured into diethyl ether/n-hexane (1:1, 400 ml). The precipitate was filtered and washed with diethyl ether, 7% disodium hydrogen phosphate solution and water and dried.

The unpurified anhydro compound was slurried in dry methylene chloride (12 ml). Under nitrogen, 2,6-lutidine (2.9 ml, 25.0 mmol) was added followed by triethylsilyl trifluoromethanesulphonate (4.1 ml, 18.1 mmol). After 20 minutes the volatiles were evaporated in vacuo and the residue taken up in n-hexane (800 ml). The precipitate was removed by filtration and the filtrate evaporated. The crude product was purified by flash chromatography on silica gel eluting with n-hexane/ethyl acetate/triethylamine mixtures to give the title compound (D5).

UV λmax (hexane) 407, 383, 364, 345, 265 and 206 nm IR νmax (thin film) 2960, 2915, 2880, 1735, 1675, 1505, 1460, 1415, 1380, 1310, 1240, 1195, 1170, 1080, 1010 and 740cm$^{-1}$. δC (67.80 MHz) [(CD$_3$)$_2$CO] 173.55, 170.48, 156.35, 154.50, 145.01, 142.17, 138.98, 135.22, 135.12, 135.02, 134.77, 134.18, 133.29, 132.83, 132.70, 132.48, 131.47, 130.63, 128.46, 127.84, 125.82, 125.71, 120.78, 102.04, 99.23, 76.69, 76.37, 76.28, 74.45, 73.78, 73.62, 73.44, 73.19, 71.15, 70.44, 68.63, 67.24, 67.18, 58.13, 53.82, 52.37, 48.12, 47.98, 45.74, 43.63, 41.24, 40.69, 40.13, 36.62, 35.16, 27.58, 19.85, 19.20, 18.89 and 11.27 ppm. Mass spectrum: FAB (3-NOBA matrix) observed mass MH$^+$ 2169. Calculated mass for $C_{117}H_{209}NO_{18}Si_9$, 2168.3.

Method B

N-(9-Fluorenylmethoxycarbonyl)-3,5,8,9,11,15,35, 2',4'-nona-O-triethylsilyl-13,14-anhydroamphotericin B (D4) (0.67 g, 0.31 mmol) was dissolved in diethyl ether (10 ml). At 0° C. and with stirring, a solution of diazomethane in diethyl ether (15 ml) was added over 0.3 hours. The diazomethane was generated from N-methyl-N-nitroso-p-toluene sulphonamide (DIAZALD) (0.29 g, 0.14 mmol); potassium hydroxide (0.11 g, 0.2 mmol); water (0.2 ml) and 2-(2-ethoxyethoxy) ethanol (0.6 ml). After stirring for a further 0.75 hours, nitrogen was bubbled through the reaction to remove excess diazomethane. The volatiles were then evaporated to leave the title compound (D5).

DESCRIPTION 6

N-(9-Fluorenylmethoxycarbonyl)-13-O-(3-chlorobenzoyl)-14-hydroxy-3,5,8,9,11,15,35,2',4'-nona-O-triethyl-silyla mphotericin B methyl ester (D6)

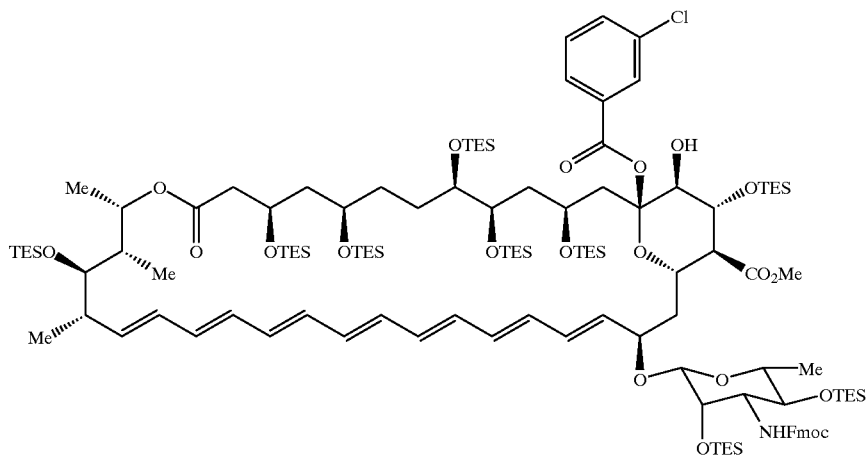

To a solution of N-(9-fluorenylmethoxycarbonyl)-3,5,8, 9,11,15,35,2',4'-nona-O-triethylsilyl-13,14-anhydro-amphotericin B methyl ester (D5) (2 g, 0.9 mmol) in dry hexane (20 ml) was added solid disodium hydrogen phosphate (0.26 g, 1.8 mmol). With ice cooling, solid m-chloroperbenzoic acid (0.21 g, 1.2 mmol) was added and the reaction was stirred for 0.5 hours. The reaction was diluted with n-hexane and washed with sodium sulphite solution (8%) and water to neutrality. The organics were dried and evaporated. The crude product was purified by flash chromatography on silica gel eluting with n-hexane/ethyl acetate/triethylamine mixtures mixtures to give the title compound (D6).

UV λmax (hexane) 405, 382 and 362.5 nm. IR νmax (thin film) 3460–3300 (br), 2960, 2910, 2880, 1735, 1505, 1460, 1415, 1375, 1240, 1110, 1080, 1005 and 740cm$^{-1}$. δC (67.80 MHz) [(CD$_3$)$_2$CO] 172.06, 171.23, 163.64, 156.30, 145.07, 144.99, 142.15, 138.55, 135.66, 135.12, 134.82, 134.50, 134.19, 133.82, 133.63, 133.44, 133.23, 133.06, 132.88, 132.68, 131.85, 131.55, 131.35, 131.12, 130.71, 129.15, 128.86, 128.46, 127.85, 125.85, 125.74, 120.78, 107.76, 98.16, 77.38, 76.34, 75.73, 74.51, 73.85, 73.67, 73.49, 73.26, 72.77, 72.06, 70.83, 69.64, 68.70, 67.60, 67.21, 58.10, 56.29, 52.44, 47.98, 47.39, 47.04, 43.72, 42.07, 41.12, 37.13, 36.16, 27.35, 19.53, 18.91, 18.31 and 11.74 ppm. Mass spectrum: FAB (3-NOBA matrix) observed mass MH$^+$ 2343. Calculated mass for C$_{124}$H$_{214}$NO$_{21}$ClSi$_9$, 2340.3.

DESCRIPTION 7

N-(9-Fluorenylmethoxycarbonyl)-14-(S)-hydroxy-13-O-methyl-3,5.8,9,11,15,35,2',4'-nona-O-triethylsilyl amphotericin B methyl ester (D7)

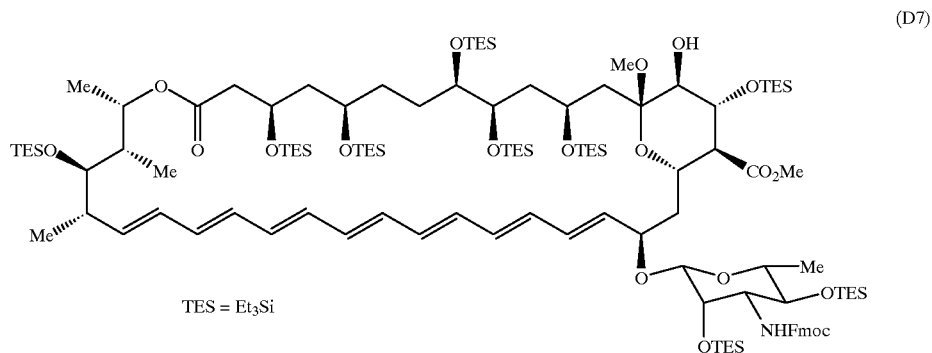

(D7)

Method A

N-(9-Fluorenylmethoxycarbonyl)-13-O-(3-chlorobenzoyl)-14-(S)-hydroxy-3,5,8,9,11,15,35,2',4'-nona-O-triethylsilyl amphotericin B methyl ester (D6) (1 g, 0.43 mmol) was dissolved in methylene chloride (12 ml) and methanol (12 ml). Under nitrogen, solid disodium hydrogen phosphate (130 mg, 0.92 mmol) was added and the mixture stirred for 22 hours. The solution was filtered and the organics evaporated. The crude product was purified by flash chromatography on silica gel using n-hexane/ethyl acetate/triethylamine mixtures.

UV λmax (hexane) 408, 384, 364 and 346 nm. IR νmax (thin film) 3450, 2960, 2915, 2880, 1740, 1505, 1460, 1415, 1380, 1310, 1240, 1195, 1165, 1080, 1010, 900, 865, 820 and 740cm$^{-1}$. δH (400 MHz) [d$_6$ acetone] 7.86 (2H, d, J 7.5 Hz), 7.70 (2H, d, J 7.2 Hz), 7.42 (2H, t, J 7.4 Hz), 7.35 (1H, t), 7.34 (1H, t), 6.73–6.58 (3H, complex), 6.48–6.09 (9H, complex), 5.93 (1H, dd, J 15.8 and 3.8 Hz), 5.46 (1H, dd, J 14.9 and 9.6 Hz), 5.30 (1H, d, J 9.9 Hz), 4.66 (1H, complex), 4.55–4.48 (2H, complex including a dd at 4.50, J 10.4 and 6.4 Hz), 4.46 (1H, s), 4.34 (1H, dd, J 10.4 and 6.4 Hz), 4.26–4.17 (4H, complex), 4.09–4.02 (2H, complex), 3.93–3.90 (2H, complex), 3.72–3.61 (6H, complex including a singlet at 3.72), 3.47 (1H, t, J 9.2 Hz), 3.40 (1H, multiplet), 3.33 (1H, multiplet), 3.15 (3H, s), 2.90 (1H, d, J 11.1 Hz), 2.69–2.40 (4H, complex including a triplet at 2.52, J 10.5 Hz and a multiplet at 2.43 Hz), 2.18 (1H, multiplet), 2.01–1.75 (10H, complex), 1.64 (1H, multiplet), 1.51 (1H, multiplet), 1.25 (3H, d, J 6.1 Hz), 1.17 (3H, d, J 6.1 Hz), 1.11–0.89 (87H, complex) and 0.83–0.55 (54H, complex) ppm. Mass spectrum: FAB (3-NOBA/Na matrix) observed mass MNa$^+$ 2239. Calculated mass for C$_{118}$H$_{213}$NO$_{20}$Si$_9$, 2216.4.

Method B

N-(9-Fluorenylmethoxycarbonyl)-3,5,8,9,11,15,35,2',4'-nona-O-triethylsilyl-13,14-anhydroamphotericin B methyl ester (D5) (197 mg, 0.091 mmol) was dissolved in methylene chloride/methanol (12 ml, 1:1). Solid disodium hydrogen phosphate (26 mg, 0.18 mmol) was added. With ice cooling solid m-chloroperbenzoic acid (20.3 mg, 0.12 mmol) was added. After stirring for 1 hour in ice, the reaction was allowed to stir at room temperature for 21 hours. The reaction was diluted with n-hexane and washed with 7% sodium sulphite solution, sodium bicarbonate solution and water. The organics were dried and evaporated. The crude product was purified by flash chromatography on silica gel using n-hexane/ethyl acetate mixtures to give the title compound (D7).

DESCRIPTION 8

N-(9-Fluorenylmethoxycarbonyl)-14-(S)-hydroxy-3,5,8,9,11,15,35,2',4'-nona-O-triethylsilylamphotericin B methyl ester (D8)

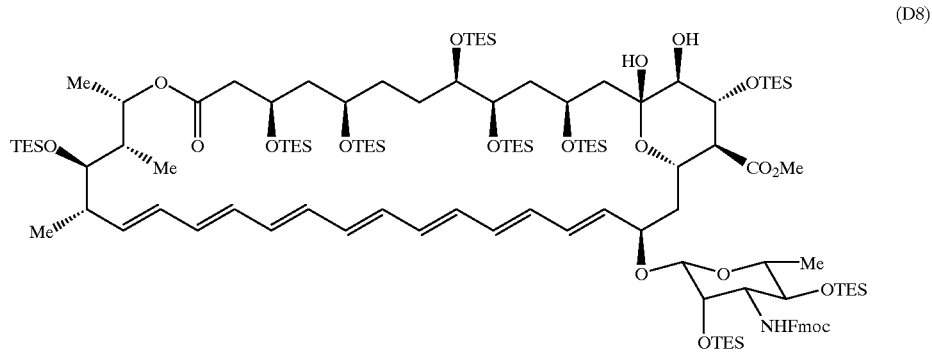

(D8)

To a solution of N-(9-fluorenylmethoxycarbonyl)-13-O-(3-chlorobenzoyl)-14-(S)-hydroxy-3,5,8,9,11,15,35,2',4'-nona-O-triethylsilylamphotericin B methyl ester (D6) (100 mg, 0.04 mmol) in n-hexane (2 ml) was added Amberlyst 15 ion-exchange resin. The solution was stirred in the dark under nitrogen for 18.5 hours. The solution was filtered and the organics washed with water. The organics were dried and evaporated. The crude product was purified by flash chromatography on silica gel using n-hexane/ethyl acetate/triethylamine mixtures.

Mass spectrum: FAB (3-NOBA/Na matrix) observed mass, MNa+ 2225. Calculated mass for $C_{117}H_{211}NO_{20}Si_9$, 2201.3.

DESCRIPTION 9

N-(9-Fluorenylmethoxycarbonyl)-3,5,8,9,11,15,35,2',4'-nona-O-trimethylsilyl-13,14-anhydroamphotericin B methyl ester (D9)

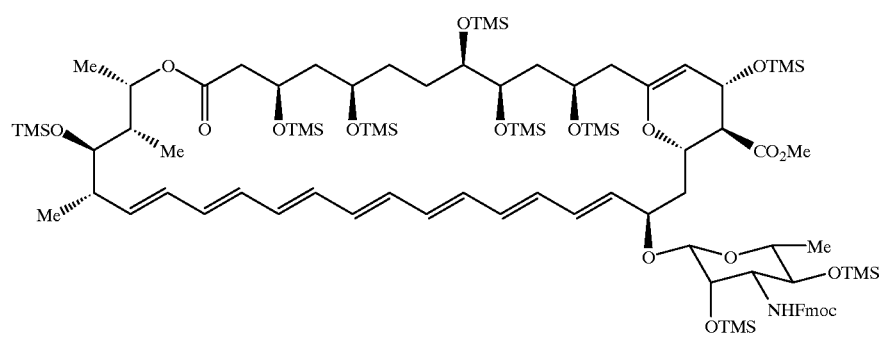

(D9)

To a slurry of N-(9-fluorenylmethoxycarbonyl)-amphotericin B methyl ester (D2) (0.17 g, 0.15 mmol) in dry methylene chloride (1.5 ml) under nitrogen was added 2,6-lutidine (0.29 ml, 2.5 mmol) followed by trimethylsilyl trifluoromethanesulphonate (0.37 ml, 1.95 mmol). After stirring at room temperature for 0.25 hours, the solution was evaporated and n-hexane (60 ml) added. The solids were triturated and removed by filtration. The organics were evaporated to give the title compound (D9).

$\delta H$ (270 MHz) ((CD$_3$)$_2$CO): 7.87 (2H,d,J 4.2 Hz), 7.70 (2H, m), 7.42 (2H,t,J 7.7 Hz), 7.32 (2H,m), 6.36 (12H,m) 5.90 (1H,dd), 5.61 (1H,dd), 4.91 (1H,m), 4.75–4.38 (3H, series of m), 4.57 (1H,s), 4.50 (1H,s), 4.39–4.09 (4H series of m), 4.09–3.78 (4H, series of m), 3.76 (3H,s), 3.63 (1H,m) 3.46 (1H,t), 3.30 (1H,m), 2.63–2.28 (5H, series of m), 2.13 (1H,d), 2.03–1.78 (5H, series of m), 1.78–1.35 (9H, series of m), 1.21 (3H,d), 1.17 (3H,d), 1.03 (3H,d), 0.97 (3H,d) and 0.13 (81H, series of m) ppm. IR vmax (CH$_2$Cl$_2$): 1730cm$^{-1}$ UV λmax (hexane): 402, 380, 362 nm.

Mass spectrum: FAB (3-NOBA/Na matrix) observed mass MNa$^+$1813, calculated for $C_{90}H_{155}NO_{18}Si_9$, 1789.92.

DESCRIPTION 10

N-(9-Fluorenylmethoxycarbonyl)-13-O-(3-chlorobenzoyl)-14-(S)-hydroxy-3,5,8,9,11,15,35,2',4'-nona-O-trimethyl-silyl amphotericin B methyl ester (D10)

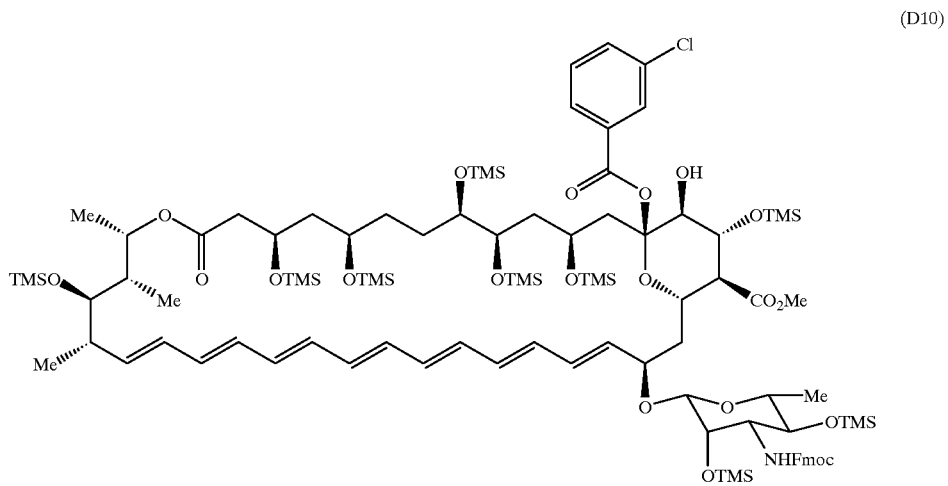

N-(9-Fluorenylmethoxycarbonyl)-3,5,8,9,11,15,35,2',4'-nona-O-trimethylsilyl-13,14-anhydroamphotericin B methyl ester (D9) (1.26 g, 0.70 mmol) was dissolved in dichloromethane (3.5 ml). At −30° C. solid m-chloroperbenzoic acid (0.122 g, 0.71 mmol) was added and the reaction allowed to reach room temperature. The reaction was diluted with hexane and washed with 7% sodium sulphite and water. The organics were evaporated.

The crude product was purified by medium pressure chromatography on silica gel using n-hexane/ethyl acetate mixtures to give the title compound (D10).

UV λmax (hexane) 404, 381, 361, 344 and 205 nm. IR νmax (thin film) 2950, 1725, 1500, 1105, 1070, 1000 and 840 cm$^{-1}$. δC (67.80 MHz) [d$_6$-acetone] 172.12, 171.02, 163.42, 156.42, 145.06, 144.90, 142.03, 137.29, 135.84, 135.03, 134.86, 134.60, 134.33, 134.15, 133.96, 133.86, 133.58, 133.34, 133.29, 132.83, 132.53, 132.22, 131.23, 130.92, 130.71, 129.13, 128.43, 127.79, 126.02, 125.93, 120.73, 106.87, 97.93, 80.57, 77.70, 75.90, 75.61, 74.43, 73.70, 73.44, 72.84, 70.86, 70.66, 69.19, 68.58, 68.47, 67.59, 67.02, 57.82, 56.60, 52.44, 47.94, 47.48, 46.99, 43.81, 42.82, 40.51, 40.44, 37.81, 35.30, 27.08, 19.68, 18.71, 17.38 and 12.18 ppm. Mass spectrum: FAB (3-NOBA matrix) observed mass MH$^+$ 1961. Calculated mass for $C_{97}H_{160}NO_{21}ClSi_9$, 1961.

DESCRIPTION 11

N-(9-Fluorenylmethoxycarbonyl)-13-O-(3-chlorobenzoyl)-14-(S)-hydroxy amphotericin B methyl ester (D11)

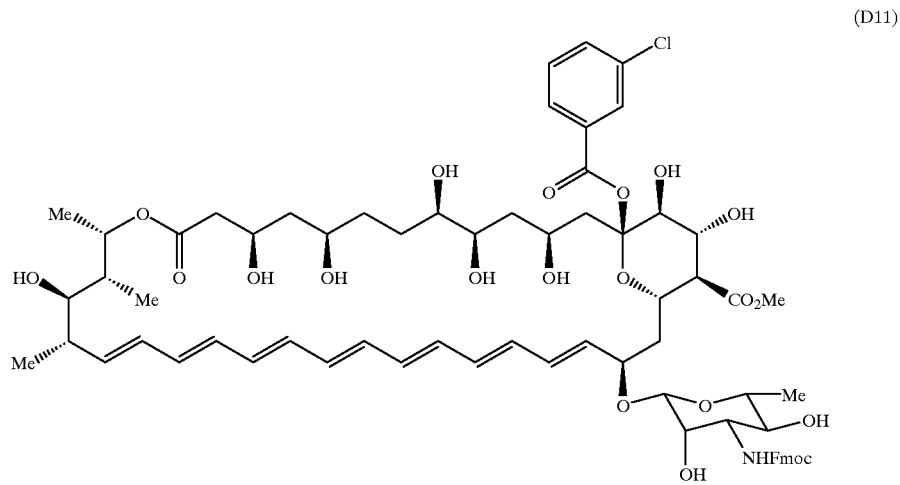

N-(9-Fluorenylmethoxycarbonyl)-13-O-(3-chlorobenzoyl)-14-(S)-hydroxy-3,5,8,9,11,35,2',4'-nona-O-trimethyl-silylamphotericin B methyl ester (D10) (161 mg, 0.08 mmol) was dissolved in dry tetrahydrofuran (2 ml) in a plastic bottle. Under nitrogen, hydrogen fluoride-pyridine solution (5 ml of a solution made from 8.5 g of 70% hydrogen fluoride pyridine reagent and 45 ml of pyridine in 180 ml of tetrahydrofuran-equivalent to 1.3M HF—6.5 mmol) was added via a plastic syringe. After stirring for four hours, the reaction was poured into diethyl ether/n-hexane (200 ml/200 ml). The precipitate was filtered and washed with diethyl ether, saturated bicarbonate, water and ether. The crude product was dried and purified by medium pressure chromatography on silica gel using methylene chloride/methanol mixtures to give the title compound (D11) and some pure material identified as the compound of Description 12, N-(9-fluorenylmethoxycarbonyl)-13-dehydroxy-13-fluoro-14-(S)-hydroxyamphotericin B methyl ester (D12).

The title compound (D11)

δH (500 MHz) [$d_5$ pyridine/$d_4$ methanol 1:1] 7.99 (1H, t, J 1.8 Hz), 7.94 (1H, d, J 7.2 Hz), 7.74 (2H, d, J 7.2 Hz), 7.59 (2H, multiplet), 7.44 (1H, multiplet), 7.29 (3H, multiplet), 7.17 (2H, t, J 7.4 Hz), 6.53–6.45 (2H, complex), 6.38–6.16 (11H, complex), 5.35 (1H, multiplet), 5.29 (1H, obscured by HOD), 5.09 (1H, d, J 9.7 Hz), 4.91 (1H, multiplet), 4.75 (1H, t, J 10.1 Hz), 4.67–4.65 (2H, complex including a singlet at 4.67), 4.52 (1H, multiplet), 4.32 (1H, multiplet), 4.24 (2H, d, J 7.3 Hz), 4.15 (1H, d, J 2.8 Hz), 4.10 (1H, t, J 7.3 Hz), 3.98 (1H, dd, J 10.3 and 2.9 Hz), 3.81 (1H, multiplet), 3.75–3.66 (5H, complex including a singlet at 3.72 and a triplet, J 10.0 Hz at 3.68), 3.50 (1H, complex), 3.28–3.22 (2H, complex), 2.83 (1H, t, J 10.7 Hz), 2.43 (1H, complex), 2.35 (1H, dd, J 16.8 and 9.8 Hz), 2.26–2.20 (2H, complex), 1.99 (1H, complex), 1.88–1.80 (4H, complex), 1.65–1.61 (2H, complex), 1.55–1.29 (8H, complex including a doublet at 1.38, J 6.1 Hz), 1.25 (3H, d, J 6.4 Hz), 1.11 (3H, d, J 6.4 Hz) and 1.04 (3H, d, J 7.1 Hz) ppm. Mass spectrum: FAB (3-NOBA/Na matrix) observed mass MNa+ 1336. Calculated mass for $C_{70}H_{88}NO_{17}Cl$, 1313.6.

DESCRIPTION 12

N-(9-Fluorenylmethoxycarbonyl)-13-dehydroxy-13-fluoro-4-(S)-hydroxyamphotericin B methyl ester (D12)

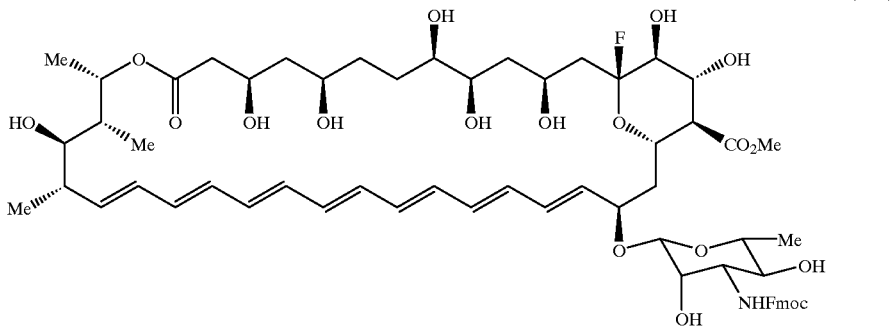

(D12)

N-(9-Fluorenylmethoxycarbonyl)-13-O-(3-chlorobenzoyl)-14-(S)-hydroxy-3,5,8,9,11,15,35,2',4'-nona-O-triethylsilylamphotericin B methyl ester (D6) (1.1 g, 0.46 mmol) was dissolved in dry tetrahydrofuran (10 ml) in a plastic bottle. Under nitrogen, hydrogen fluoride.pyridine solution (18 ml of a solution made from 15.61 g of 70% hydrogen fluoride.pyridine reagent and 92 ml of pyridine made up to 250 ml with tetrahydrofuran—equivalent to 2.1M HF—36.8 mmol) was added via a plastic syringe. After stirring for 25 hours the reaction was poured into diethyl ether/n-hexane (1:1, 800 ml). The precipitate was filtered and washed with diethyl ether, 7% disodium hydrogen phosphate solution and water and dried. The crude product was purified by medium pressure chromatography on silica gel eluting with methylene chloride/methanol mixtures.

U.V. λmax (methanol) 404.9, 381.6, 362.5 and 344 nm. δC (67.80 MHz) [$d_5$ pyridine/$d_4$ methanol 1:1] 172.56, 172.16, 158.15, 145.10, 144.96, 142.10, 137.63, 136.36, 134.78, 134.22, 134.13, 133.88, 133.62, 133.23, 132.78, 130.99, 128.49, 127.91, 126.14, 126.09, 120.74, 116.88 and 113.51 (doublet J 227.3 Hz), 98.97, 78.95, 76.40, 75.47, 75.36, 75.04, 72.24, 71.72, 71.34, 71.19, 70.65, 68.79, 68.58, 68.32, 67.37, 58.46, 56.52, 52.55, 48.83, 48.19, 44.82, 43.72, 43.12, 41.53, 41.10, 37.92, 36.34, 31.25, 19.08, 18.55, 17.50 and 12.61 ppm. Mass spectrum: FAB (3-NOBA-Na matrix) observed mass MNa+1200, MNa+-HF 1180. Calculated mass for $C_{63}H_{84}NO_{19}F$, 1177.6.

DESCRIPTION 13

N-(9-Fluorenylmethoxycarbonyl)-14-(S)-hydroxy-13-O-methylamphotericin B methyl ester (D13)

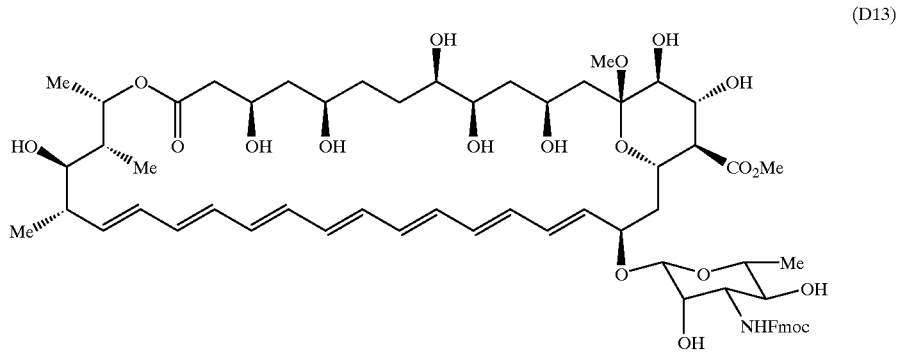

(D13)

N-(9-Fluorenylmethoxycarbonyl)-14-(S)-hydroxy-13-O-methyl-3,5,8,9,11,15,35,2',4'-nona-O-triethylsilyl-amphotericin B methyl ester (D7) (314 mg, 0.14 mmol) was dissolved in dry tetrahydrofuran (5 ml) in a plastic bottle. Under nitrogen, hydrogen fluoride.pyridine solution (5.7 ml of a solution made from 14.3 g of 70% hydrogen fluoride.pyridine reagent and 90 ml of pyridine made up to 250 ml with tetrahydrofuran—equivalent to 2M HF—11.4 mmol) was added via a plastic syringe. After stirring for 20 hours the reaction was poured into diethyl ether (400 ml). The precipitate was filtered and washed with diethyl ether and dried.

UV λmax (methanol) 406.2, 382.5, 364 and 346 nm IR νmax (KBr disc) 3400, 2940, 1725, 1540, 1455, 1310, 1190, 1170, 1070, 1015, 765 and 745cm$^{-1}$. δH (400 MHz) [d$_5$ pyridine/d$_4$ methanol 1:1] 7.84 (2H, d, J 7.5 Hz), 7.71 (2H, t, J 8.2 Hz), 7.41 (2H, t, J 7.3 Hz), 7.29 (2H, t, J 7.4 Hz), 6.55–6.32 (12H, complex), 6.09 (1H, dd, J 14.4 and 6.2 Hz), 5.66 (1H, dd, J 14.3 and 9.3 Hz), 5.40 (1H, multiplet), 4.84 (1H, multiplet), 4.78 (1H,s), 4.53 (1H, dd, 10.2 and 9.4 Hz), 4.46 (1H, complex), 4.39–4.33 (4H, complex), 4.28–4.21 (2H, complex), 4.06 (1H, dd, J 10.2 and 2.8 Hz), 3.98 (1H, complex), 3.80–3.75 (4H, complex including a singlet at 3.78), 3.63 (1H, d, J 9.2 Hz), 3.58 (1H, multiplet), 3.53–3.49 (2H, complex), 3.42 (1H, complex), 3.33 (3H, s), 2.85 (1H, t, J 10.7 Hz), 2.56–2.50 (2H, complex), 2.41 (1H, dd, J 16.6 and 3.6 Hz), 2.30 (1H, multiplet), 2.19 (1H, multiplet), 2.07–1.85 (5H, complex), 1.78–1.60 (6H, complex), 1.49 (3H, d, J 6.1 Hz), 1.33 (3H, d, J 6.3 Hz), 1.24 (3H, d, J 6.6 Hz) and 1.14 (3H, d, J 7.1 Hz) ppm. Mass spectrum: FAB (thiodiethanol/Na matrix) observed mass MNa$^+$ 1212. Calculated mass for $C_{64}H_{87}NO_{20}$, 1189.6.

DESCRIPTION 14

N-(9-Fluorenylmethoxycarbonyl)-13,14-anhydroamphotericin B methyl ester (D14)

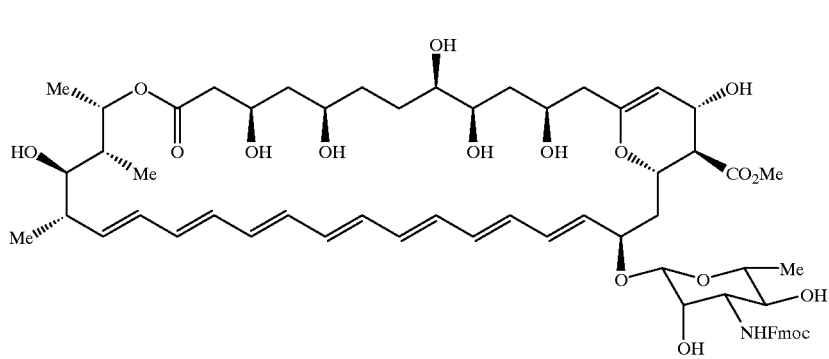

(D14)

To N-(9-fluorenylmethoxycarbonyl)-3,5,8,9,11,15,35,2',4'-nona-O-trimethylsilyl-13,14-anhydroamphotericin B methyl ester (D9) (0.77 g, 0.42 mmol) in dry tetrahydrofuran (10 ml) under nitrogen in a plastic bottle was added, with a plastic syringe, hydrogen fluoride.pyridine solution (26 ml of a solution made from 8.5 g of 70% hydrogen fluoride.pyridine reagent and 45 ml of pyridine in 180 ml of tetrahydrofuran—equivalent to 1.3M HF—34 mmol). After stirring for 4 hours, the solution was poured into a 1:1 mixture of diethyl ether/n-hexane (2L). The precipitate was filtered and washed with diethyl ether, saturated sodium bicarbonate solution and water and dried to give the title compound (D14).

The compound was purified by silica-gel chromatography using methylene chloride/methanol mixtures under medium pressure.

δH (400 MHz) (1:1 $d_5$ pyridine:$d_4$ methanol): 7.84 (2H,d, J 7.5 Hz), 7.72 (2H,d,J 7.2 Hz), 7.42 (2H,t,J 7.4 Hz), 7.31 (2H,t, J 7.4 Hz), 6.55–6.30 (12H, complex), 6.07 (1H,dd, J 14.1 and 7.6 Hz), 5.60 (1H,dd,J 13.9 and 9.8 Hz), 5.47 (1H,m), 4.92 (1H,m) 4.81–4.71 (3H,complex), 4.50–4.41 (2H, complex), 4.38 (2H,d,J 7.2 Hz), 4.3–4.2 (2H, complex), 4.21 (1H,m), 4.05 (1H,dd, J 10.2 and 2.8 Hz), 3.95 (1H,t,J 9.6 Hz), 3.86 (1H,d,J 9.6 Hz), 3.78 (3H,s), 3.75 (1H,m), 3.56 (1H,m), 3.44 (1H,m), 3.42 (1H,m), 2.82 (1H,dd J 10.5 and 9.3 Hz), 2.55 (1H,m), 2.48 (1H,dd,J 17.1 and 9.7 Hz), 2.33 (1H,m), 2.29 (2H,m), 2.18 (2H,m), 2.12 (1H,m), 1.98 (2H, complex), 1.80 (1H,m), 1.7–1.5 (4H, complex), 1.52 (1H, m), 1.47 (3H,d,J 6.1 Hz), 1.34 (3H,d,J 6.4 Hz), 1.25 (3H,d,J 6.5 Hz) and 1.15 (3H,d,J 7.1 Hz) ppm. IR νmax (nujol): 1720cm$^{-1}$. UV λmax (ethanol): 407, 384, 365 nm. Mass spectrum: FAB (3-NOBA/Na matrix) observed mass MNa$^+$ 1164, calculated for $C_{63}H_{83}NO_{18}$, 1141.56.

DESCRIPTION 15

N-(9-Fluorenylmethoxycarbonyl)-14-(R)-hydroxy-13-O-methylamphotericin B methyl ester (D14)

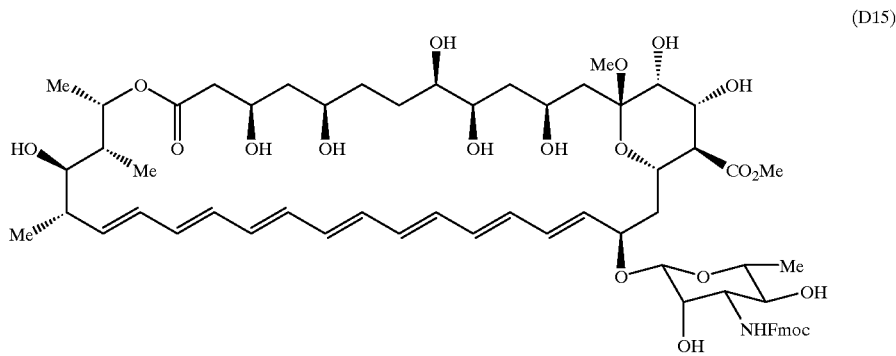

(D15)

N-(9-Fluorenylmethoxycarbonyl)-13,14-anhydro-amphotericin B methyl ester (D14) (98 mg, 0.085 mmol) was dissolved in dry tetrahydrofuran (1.5 ml). After cooling to −60° C., and under nitrogen, m-chloroperbenzoic acid (19 mg, 0.11 mmol) was added in tetrahydrofuran. The reaction temperature was maintained between −60° C. and −20° C. After thirty minutes, methanol (1 ml) was added and the mixture precipitated in diethyl ether (250 ml). The solid was filtered and washed with ether. The product was purified by means of medium pressure chromatography on silica gel using chloroform, methanol, ammonia mixtures to give the title compound (DI5).

δH (270 MHz) [$d_5$ pyridine/$d_4$ methanol, 1:1] Characteristic signals include 7.85 (2H,d,J 7.7 Hz), 7.71 (2H,t,J 6.6 Hz), 7.42 (2H,t,J 7.4 Hz), 7.29 (2H,t,J 7.6 Hz), 6.57–6.31 (12H,complex), 6.11 (1H,dd,J 15.1 and 5.5 Hz), 5.70 (1H, dd,J 14.6 and 8.8 Hz), 4.79 (1H,s), 4.62 (1H,dd,J 11.0 and 3.3 Hz), 4.38 (2H,d,J 7.2 Hz), 4.09 (1H,dd,J 10.0 and 2.9 Hz), 3.80 (3H,s), 3.27 (3H,s), 3.16 (3H,t,J 10.9 Hz), 2.41 (1H,dd,J 16.6 and 3.7 Hz), 1.50 (3H,d,J 5.8 Hz), 1.33 (3H,d,J 6.3 Hz), 1.25 (3H,d,J 6.6 Hz) and 1.14 (3H,d,J 7.1 Hz). Mass spectrum: FAB (thiodiethanol/Na matrix); Observed mass, MNa$^+$ 1212.5. Calculated mass for $C_{64}H_{87}NO_{20}$, 1189.6.

DESCRIPTION 16

N-(9-Fluorenylmethoxycarbonyl) amphotericin B, allyl ester (D16)

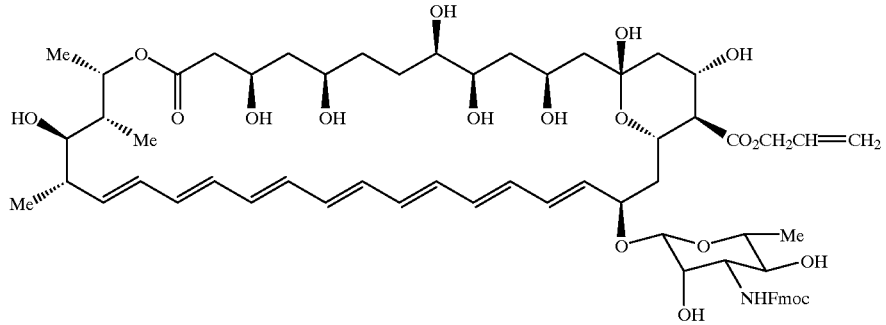

N-(9-Fluorenylmethoxycarbonyl) amphotericin B (D1) (1.24 g, 1.08 mmol) in dimethylformamide (40 ml) was sequentially treated with methanol (4 ml), diisopropylethylamine (0.80 ml, 4.52 mmol) and allyl bromide (4 ml), and the mixture stirred in a sealed flask for 4 hours. The solution was added to ether (2l) and the precipitate filtered and washed with ether. The solids were then stirred thoroughly in water for 5 minutes and refiltered to give a residue which was purified by chromatography on silica, eluting with methylene chloride: methanol (10:1) to give the title product (D16) (0.53 g).

λmax (MeOH) 404 (ε130,000), 381 (ε116,000), 362 (ε72,000) nm. νmax (nujol) 3400, 1725, 1705cm-1. (CD$_3$OD). Characteristic signals include: δ$^1$H (270 MHz) 1.12 (3H,d, J7.15 Hz), 1.20 (3H,d, J6.3 Hz), 1.31 (3H,d, J6.6 Hz), 1.42 (3H,d), 4.33 (2H,d, J6.3 Hz), 4.69 (1H,s), 5.55 (1H,m), 6.01 (1H,m), 7.30 (2H,t), 7.41 (2H,t, J7.4 Hz), 7.69 (2H,m), 7.83 (2H,d, J7.4 Hz). δ$^{13}$C (68 MHz) (CD$_3$OD:C$_5$D$_5$N; 1:1) 12.57, 17.33, 18.49, 19.18, 31.52, 36.35, 38.93, 40.89, 41.41, 42.81, 44.08, 44.83, 45.26, 47.57, 48.25, 58.32, 58.46, 67.58, 68.50, 66.79, 67.22, 68.87, 69.84, 70.64, 71.50, 71.95, 72.47, 74.98, 75.42, 76.29, 77.45, 79.33, 98.80, 99.04, 118.63, 120.83, 126.23, 128.03, 128.61, 130.61, 133.10, 133.39, 133.53, 133.71, 133.94, 134.00, 134.13, 134.29, 134.40, 134.95, 135.03, 137.35, 137.59, 142.26, 145.10, 145.20, 158.30, 172.52, 173.93. Mass spectrum: (FAB; NOBA-Na matrix). Found: M+Na$^+$, 1208. C$_{65}$H$_{87}$NO$_{19}$ requires M, 1185.6.

DESCRIPTION 17

N-(9-Fluorenylmethoxycarbonyl)-3,5,8,9,11,15,35,2',4'-nona-O-trimethylsilyl-13,14-anhydroamphotericin B, allyl ester (D17)

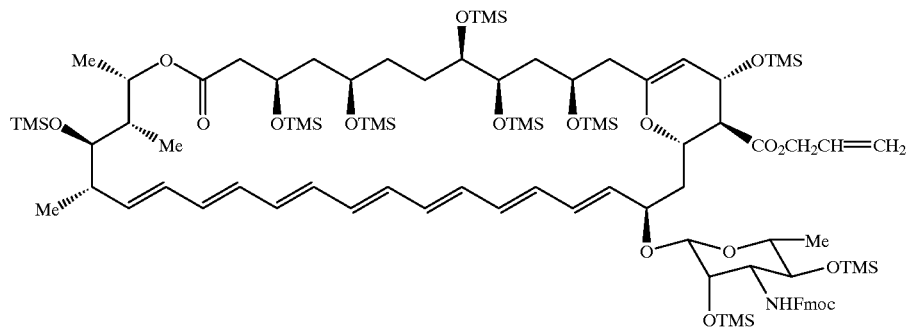

To a slurry of N-(9-fluorenylmethoxycarbonyl) amphotericin B, allyl ester (D16) (0.22 g, 0.19 mmol) in dry methylene chloride (3 ml) was added 2,6-lutidine (0.36 ml, 3.10 mmol) and trimethylsilyl triflate (0.46 ml, 2.38 mmol). After 15 mins at room temperature, the solution was evaporated and hexane (75 ml) added. Solids were triturated and filtered off, and further washed with hexane (40 ml). The hexane solutions were combined and evaporated to give the title product (D17), used without further purification (0.31 g).

λmax (hexane) 402, 381, 362 nm. νmax (hexane) 1730cm$^{-1}$. δ$^1$H (270 MHz) ((CD$_3$)$_2$CO). Characteristic signals include: 0.96 (3H,d, J6.9 Hz), 1.03 (3H,d, J6.6 Hz), 1.17 (3H,d, J6.3 Hz), 1.20 (3H,d, J6.05 Hz), 2.59 (1H,dd, Jmax 8.8 Hz), 3.46 (1H,t, J9.7 Hz), 4.68 (1H,s), 4.90 (1H,m), 5.28 (1H,d, J9 Hz), 5.43 (1H,d, J14 Hz), 5.62 (1H,dd, J 15,9 Hz), 5.86 (1H,dd, J18, 9 Hz), 6.0 (1H,m), 7.35 (2H,t, J7.4 Hz), 7.42 (2H,t, J7.4 Hz), 7.72 (2H,m), 7.87 (2H,d, J7.4 Hz). $\delta^{13}C$ (68 MHz) ($(CD_3)_2CO$) 11.95, 18.48, 18.75, 19.47, 28.07, 35.10, 37.32, 39.12, 41.47, 43.6, 42.36, 43.58, 47.77, 48.03, 53.83, 57.96, 66.06, 67.13, 67.28, 68.55, 69.16, 70.93, 72.37, 73.00, 73.15, 73.82, 74.52, 75.55, 76.27, 78.56, 98.99, 102.85, 118.90, 120.79, 126.05, 127.84, 128.49, 130–135 (m), 135.74, 138.12, 142.12, 145.01, 145.12, 153.48, 156.49, 170.88, 172.79. Mass spectrum: (FAB; NOBA-Na matrix). Found: MNa$^+$, 1839.5. $C_{92}H_{157}NO_{18}Si_9$ requires M, 1815.9.

DESCRIPTION 18

N-(9-Fluorenylmethoxycarbonyl)-13,14-anhydroamphotericin B allyl ester (D18)

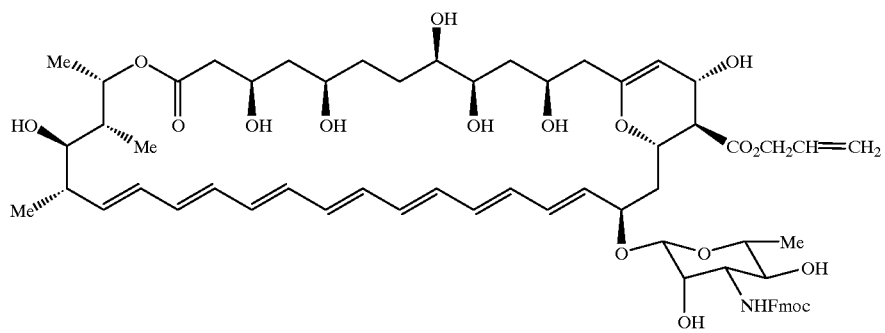

To N-(9-Fluorenylmethoxycarbonyl)-3,5,8,9,11,15,35,2',4'-nona-O-trimethylsilyl-13,14-anhydroamphotericin B, allyl ester (D17) (2.5 g, 1.37 mmol) in dry tetrahydrofuran (40 ml) under nitrogen in a plastic bottle was added, with plastic syringe, a solution of pyridinium hydrofluoride in pyridine: tetrahydrofuran (53.4 ml 2.06M solution (10 mmol); stock solution made up from 14.64 g 70% hydrogen fluoride in pyridine, pyridine (90 ml) and tetrahydrofuran (to total volume of 250 ml)). After stirring 4 h at room temperature, the solution was poured into hexane:ether (1:1) (4l). The precipitate was filtered and washed with ether (1l). Drying under vacuum gave 1.44 g residue which was chromatographed on silica (50 g; elution with methylene chloride:methanol (12:1)) to give the title product (D18) (0.94 g).

λmax (MeOH) 407 (ε149,000), 383 (134,000), 364 (83,000)nm. νmax (nujol) 3400–3200, 1710cm$^{-1}$. $\delta^1H$ (400 MHz) ($CD_3OD$: $C_5D_5N$; 1:1). Characteristic signals include 1.16 (3H,d, J7.15 Hz), 1.25 (3H,d, J6.6 Hz), 1.34 (3H,d, J6.3 Hz), 1.48 (3H,d, J6.05 Hz), 2.49 (1H,dd, J17.0, 9.6 Hz), 2.86 (1H,br t, 'J'10 Hz), 3.58 (1H,m), 3.78 (1H,t, 'J'9 Hz), 3.87 (1H,m), 3.97 (1H,m), 4.07 (1H,dd, J10.2, 2.75 Hz), 4.38 (2H,d, J7.15 Hz), 4.94 (1H, br s), 5.27 (1H,d, J11.8 Hz), 5.47 (1H,dd, J17.2, 1.4 Hz), 5.61 (1H,m), 6.06 (2H, m), 7.30 (2H, t, J7.4 Hz), 7.42 (2H, t, J7.4 Hz), 7.72 (2H,m), 7.85 (2H,d, J7.4 Hz) Mass spectrum: (FAB: TDE-Na matrix). Found: MNa$^+$, 1191.0. $C_{65}H_{85}NO_{18}$ requires M, 1167.6. $\delta^{13}C$ ($CD_3OD$: $C_5D_5N$; 1:1) (68 MHz) 12.58, 17.71, 18.58, 18.99, 31.32, 36.35, 37.76, 40.80, 41.87, 43.18, 44.48, 43.59, 48.05, 54.50, 58.34, 66.19, 67.40, 67.51, 68.68, 69.14, 70.87, 71.40, 71.72, 72.50, 73.08, 74.93, 75.39, 75.50, 76.75, 78.84, 99.50, 104.24, 118.80, 120.74, 126.13, 127.91, 128.49, 131.68–137.63 (m), 142.09, 144.94, 145.07, 152.69, 158.15, 172.07, 173.55.

DESCRIPTION 19

N-(9-Fluorenylmethoxycarbonyl)-14-(R)-hydroxy amphotericin B, allyl ester (D19)

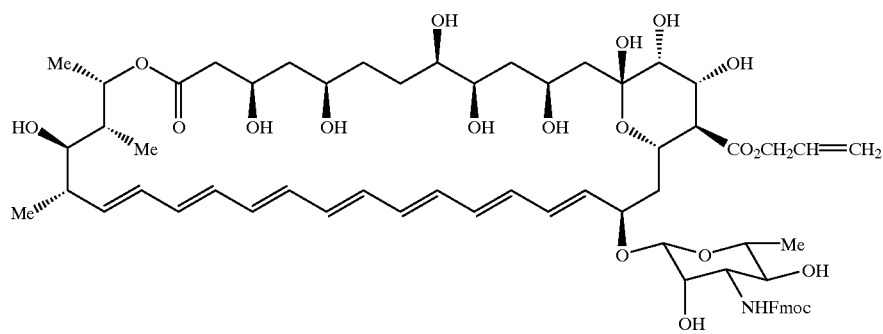

N-(9-Fluorenylmethoxycarbonyl)-13,14-anhydro-amphotericin B, allyl ester (D18) (1.12 g, 0.93 mmol) in tetrahydrofuran (100 ml) was treated with water (7 ml) and then cooled to −20°.

m-Chloroperbenzoic acid (0.20 g, 1.18 mmol) was added, and the solution was allowed to warm to room temperature over ½ h. After ½ h further, ethyl acetate (200 ml) was added and the organic phase washed with dilute sodium sulphite solution. Further tetrahydrofuran was added to the ethyl acetate layer to re-obtain a clear solution which was water washed, dried ($Na_2SO_4$) and evaporated to give the crude product, purified by chromatography on silica (methylene chloride (6): methanol (1): tetrahydrofuran (0.5) eluant) to give D19 (0.84 g).

λmax (MeOH) 406 (ε142,000), 382 (127,000),363 (78,000)nm. νmax (nujol) 3300–3400, 1720 (sh), 1705cm$^{-1}$. $\delta^1H$ (400 MHz) ($CD_3OD$: $C_5D_5N$; 1:1). Characteristic signals include 1.18 (3H,d, J7.3 Hz), 1.25 (3H,d, J6.4 Hz), 1.36 (3H,d, J6.4 Hz), 1.39 (3H,d, J6.1 Hz), 2.35 (1H,dd, J16.9, 2.6 Hz), 2.49 (1H,dd, J16.9, 9.7 Hz), 3.17 (1H,t, J10.8 Hz), 3.77 (1H, 't', 'J'10 Hz), 3.89 (1H,d, J2.9 Hz), 4.09 (1H,dd, J10.2, 2.9 Hz), 5.24 (1H,dd, J10.5, 1.2 Hz),5.47 (2H,m), 5.63 (1H,m), 6.04 (1H,m), 7.30 (2H,t, J7.3 Hz), 7.42 (2H,t, J7.4 Hz), 7.71 (2H,m), 7.84 (2H,d, J7.5 Hz). $\delta^{13}C$ (68 MHz) ($CD_3OD$: $C_5D_5N$; 1:1) 12.62, 17.34, 18.60, 19.08, 31.55, 36.38, 38.60, 41.04, 41.26, 42.84, 43.26, 44.89, 43.97, 48.19, 52.15, 58.38, 65.93, 67.37, 66.68, 68.68, 69.39, 70.30, 70.49, 71.47, 71.91, 72.30, 72.84, 74.96, 75.28, 76.37, 77.13, 79.07, 98.88, 100.42, 118.37, 120.74, 126.15, 127.91, 128.49, 130.52, 133.00–134.88(m), 142.09, 144.99, 145.10, 158.17, 172.33, 174.10. Mass spectrum: (FAB: TDE-Na matrix). Found: MNa$^+$, 1225.0. $C_{65}H_{87}NO_{20}$ requires M, 1201.6.

DESCRIPTION 20

N-(19-Fluorenylmethoxycarbonyl)-14-(R)-hydroxyamphotericin B methyl ester (D20)

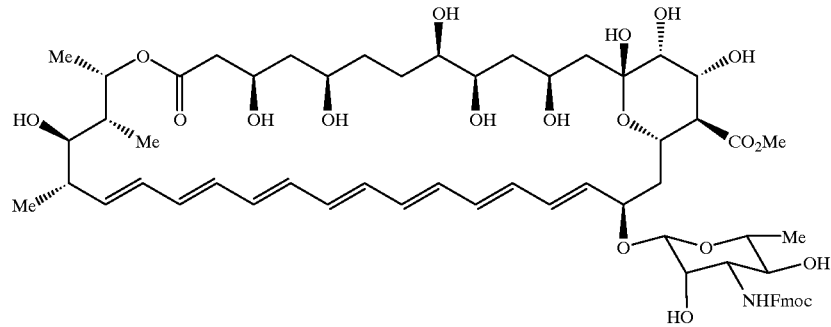

N-(9-Fluorenylmethoxycarbonyl)-13,14-anhydro-amphotericin B methyl ester (D14) (100 mg, 0.088 mmol) was dissolved in tetrahydrofuran/water (5:1, 5.5 ml). At −30° C., m-chloroperbenzoic acid (18 mg, 0.115 mmol) in tetrahydrofuran (0.2 ml) was added. The reaction was allowed to reach room temperature. After 1 hr the reaction was poured into diethyl ether (250 ml). The precipitate was filtered and washed with ether. The crude product was purified by medium pressure chromatography on silica gel using chloroform/methanol/ ammonia mixtures to give the title compound (D20).

Mass spectrum: FAB (thiodiethanol/Na matrix) observed mass, MNa$^+$ 1198.8. Calculated mass for $C_{63}H_{85}NO_{20}$, 1175.8.

DESCRIPTION 21

N-(9-Fluorenylmethoxycarbonyl)-16-decarboxy-16-hydroxymethyl-13,14-anhydroamphotercin B (D21)

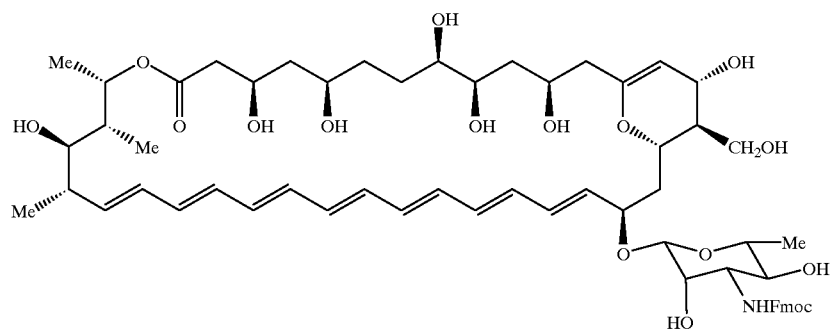

To a solution of N-(9-fluorenylmethoxycarbonyl)-13,14-anhydroamphotericin B methyl ester (D14) (0.70 g, 0.61 mmol) in methanol/tetrahydrofuran (15 ml, 3:1) at room temperature was added portionwise sodium borohydride (0.58 g, 15.3 mmol).

After 0.3 hours the reaction was quenched by adding saturated sodium bicarbonate solution (1 ml) and then poured into saturated sodium bicarbonate solution (800 ml). The precipitate was filtered and washed withwater to neutrality and dried to give the title compound, (D21).

UV λmax (methanol) 406, 383, 364 and 346 nm. IR νmax (KBr disc) 3411, 3013, 2932, 1725, 1641, 1539, 1440, 1321, 1305, 1195, 1151, 1112, 1067, 1011, 969, 851, 825 and 534 cm$^{-1}$. δH (400 MHz) [d$_5$ pyridine:d$_4$ methanol, 1:1]. 6.53–6.32 (12H, complex), 6.10 (1H, dd, J 15.4 and 5.7 Hz), 5.69 (1H, dd, J 14.5 and 9.2 Hz), 5.37 (1H, multiplet), 4.84 (1H, multiplet), 4.71 (1H, d, J 0.8 Hz), 4.58 (1H, dd, J 11.0 and 3.3 Hz), 4.44 (1H, complex), 4.33 (1H, complex), 4.24 (1H, complex), 4.22 (1H, d, J 3.4 Hz), 4.16 (1H, dd, J 3.2 and 0.6 Hz), 3.97 (1H, complex), 3.78 (3H, s), 3.78 (1H, complex), 3.53–3.46 (4H, complex), 3.26 (3H, s), 3.14 (1H, t, J 10.8 Hz), 2.82 (1H, dd, J 9.2 and 3.1 Hz), 2.54 (2H, complex including dd J 16.8 and 8.4 Hz), 2.41 (1H, dd 16.7 and 3.9 Hz), 2.18–1.97 (6H, complex), 1.86–1.81 (2H, complex), 1.75–1.60 (5H, complex), 1.45 (3H, d, J 5.8 Hz), 1.33 (3H, d, J 6.3 Hz), 1.25 (3H, d, J 6.6 Hz) and 1.14 (3H, d, J 7.1 Hz) ppm. Mass spectrum: FAB (3-NOBA/Na matrix) observed mass MNa$^+$ 1136, calculated for C$_{62}$H$_{83}$NO$_{17}$ 1113.57.

DESCRIPTION 22

N-9-Fluorenylmethoxycarbonyl-16-decarboxy-16-hydroxymethyl-14-(R)-hydroxyamphotericin B (D22)

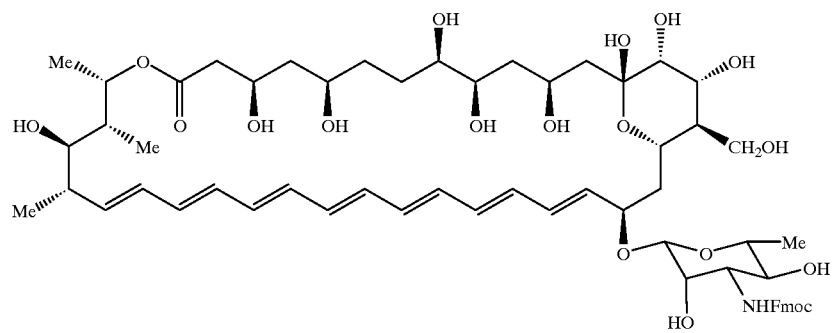

N-(9-Fluorenylmethoxycarbonyl)-16-decarboxy-16-hydroxymethyl-13,14-anhydroamphotericin B (D21) (126 mg, 0.11 mmol) was dissolved in tetrahydrofuran/water (3:1, 6 ml). At room temperature, m-chloroperbenzoic acid (23.5 mg, 0.14 mmol) in tetrahydrofuran (0.4 ml) was added. After stirring for 0.5 hours the reaction was poured into diethyl ether (800 ml) and the precipitate was filtered. After washing with diethyl ether and drying, the crude product was purified by medium pressure chromatography on silica gel using firstly chloroform/methanol/ammonia mixtures and then methylene chloride/methanol mixtures to give the title compound (D22).UV λmax (methanol) 406, 382, 363 and 345 nm. IR νmax (KBr disc) 3422, 3013, 2924, 2854, 1716, 1693, 1617, 1570, 1509, 1450, 1382, 1298, 1250, 1184, 1072, 1011, 972 and 738cm$^{-1}$. δH (400 MHz) [d$_5$ pyridine/d$_4$ methanol 1:1] 7.84 (2H, d, 7.6 Hz), 7.71 (2H, t, 7.7 Hz), 7.42 (2H, t, 7.4 Hz), 7.32 (2H, t, 7.4 Hz), 6.63 (2H, multiplet), 6.48–6.31 (11H, complex), 5.62 (1H, multiplet), 5.47 (1H, dd, J 14.8 and 10.1 Hz), 4.94 (1H, s), 4.75–4.70 (3H, complex), 4.50–4.37 (4H, complex), 4.26–4.20 (2H, complex), 4.15–4.06 (3H, complex), 3.95 (1H, multiplet), 3.89–3.86 (2H, complex including a doublet, J 7.3 Hz), 3.76 (1H, t, J 9.6 Hz), 3.57 (1H, multiplet), 3.43–3.36 (2H, complex), 2.72 (1H, multiplet), 2.57–2.32 (5H, complex), 2.12–1.99 (5H, complex), 1.80–1.50 (6H, complex), 1.46 (3H, d, J 6.1 Hz), 1.35 (3H, d, J 6.4 Hz), 1.24 (3H, d, J 6.4 Hz) and 1.16 (3H, d, J 7.1 Hz) ppm. Mass spectrum: FAB (thiodiethanol/Na matrix) observed mass MNa$^+$ 1170.6. Calculated mass for C$_{62}$H$_{85}$NO$_{19}$, 1147.6.

EXAMPLE 1

13-Dehydroxy-13-fluoro-14-(S)-hydroxyamphotericin B methyl ester (E1)

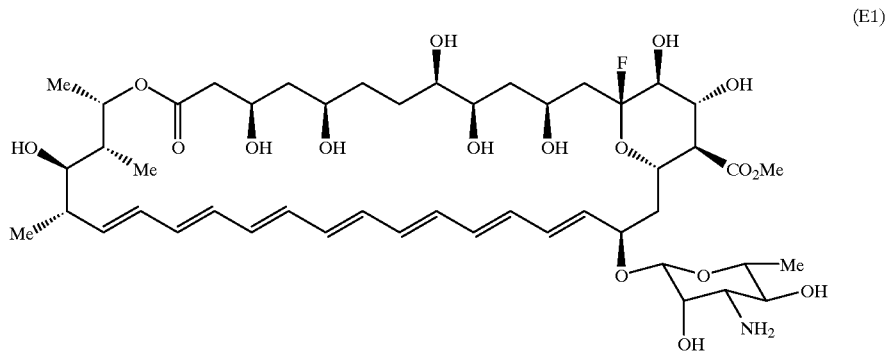
(E1)

To a solution of N-(9-fluorenylmethoxycarbonyl)-13-dehydroxy-13-fluoro-14-(S)-hydroxyamphotericin B methyl ester (D12) (0.11 g, 0.093 mmol) in dimethylsulphoxide/methanol (3:1, 4 ml) was added piperidine (28 μl, 0.28 mmol), under nitrogen. After stirring for 1 hour the reaction was poured into diethyl ether (400 ml). The precipitate was filtered and washed with diethyl ether and dried to give the title compound (E1).

U.V. λmax (methanol) 405.5, 382, 363 and 345 nm. I.R. ν(KBr disc) 3380, 2920, 1725, 1635, 1600, 1550, 1440, 1380, 1305, 1275, 1180, 1160, 1060, 1010, 890, 850 and 790cm$^{-1}$. δH (400 MHz) [d$_5$ pyridine/d$_4$ methanol 1:1] 6.62–6.32 (12H, complex), 6.22 (1H, dd J 15.5 and 8.2 Hz), 5.56–5.50 (2H, complex), 4.78–4.73 (2H, complex), 4.68 (1H,s), 4.54 (1H, multiplet), 4.51–4.45 (2H, complex), 4.14 (1H, d, J 2.9 Hz), 3.98 (1H multiplet), 3.89 (1H, multiplet), 3.78 (3H,s), 3.58 (1H, dd, J 23.4 and 9.3 Hz), 3.51–3.32 (4H, complex), 2.90 (1H, t, J 10.8 Hz), 2.82 (1H, dd, J 9.1 and 3.1 Hz), 2.59–2.46 (3H, complex including dd at 2.50, J 16.9 and 9.4 Hz), 2.35 (1H, dd, J 16.8 and 2.9 Hz), 2.24 (1H, multiplet), 2.11–1.92 (5H, complex), 1.79–1.53 (6H, complex), 1.44 (3H, d, J 5.7 Hz), 1.35 (3H, d, J 6.4 Hz), 1.24 (3H, d, J 6.5 Hz), and 1.16 (3H, d, J 7.1 Hz) ppm. Mass spectrum: FAB (thiodiethanol/NaCl matrix) MNa$^+$978, MNa$^+$-HF 958. Calculated mass for $C_{48}H_{74}NO_{17}F$, 955.5.

EXAMPLE 2

14-hydroxyamphotericin B methyl ester (E2)

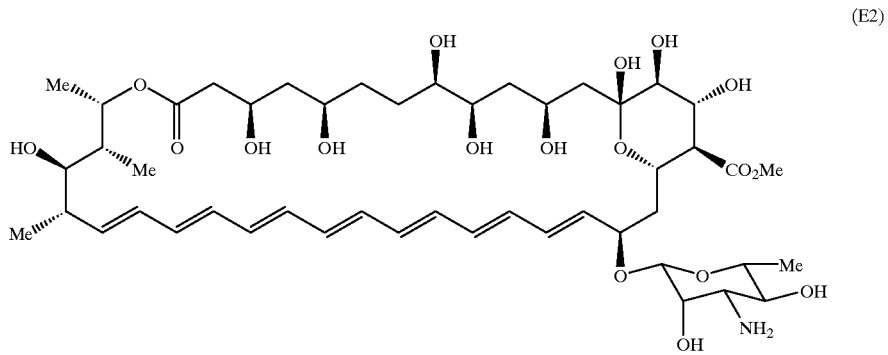
(E2)

13-Dehydroxy-13-fluoro-14-(S)-hydroxyamphotericin B methyl ester (E1) (60 mg, 0.063 mmol) was dissolved in tetrahydrofuran/water (2.5 ml, 3:1). Under nitrogen, solid camphorsulphonic acid (20 mg, 0.086 mmol) was added. After stirring for 0.5 hours a further portion of camphorsulphonic acid (9 mg, 0.038 mmol) was added. After stirring for a further 1.5 hours, triethylamine (37 μl, 0.27 mmol) was added and the reaction poured into diethyl ether (400 ml). The solid was filtered and washed with diethyl ether and dried. The crude product was purified by flash chromatography on silica gel using chloroform, methanol and ammonia mixtures.

δH (400 MHz) [d$_5$ pyridine/d$_4$ methanol 1:1] 6.67–6.26 (13H, complex), 5.63 (1H, multiplet), 5.50 (1H, dd, J 14.6 and 10.2 Hz), 4.90 (1H, multiplet), 4.80–4.75 (2H, complex including singlet at 4.74), 4.64 (1H, multiplet), 4.52–4.42 (2H, complex including dd at 4.49, J 10.4 and 9.4 Hz), 4.27 (1H, d, J 3.2 Hz), 3.95 (1H, multiplet), 3.86 (1H, multiplet), 3.75 (3H,s), 3.64 (1H, t, J 9.5 Hz), 3.53–3.49 (1H, multiplet), 3.39–3.36 (3H, complex including d at 3.38, J 9.3 Hz), 3.12 (1H, dd, J 9.7 and 3.2 Hz), 2.79 (1H, t, J 10.6 Hz), 2.57–2.39 (3H, complex), 2.35 (1H, dd, J 16.8 and 2.7 Hz), 2.25 (1H, multiplet), 2.13–1.86 (5H, complex), 1.79–1.50 (6H, complex), 1.45 (3H, d, J 6.1 Hz), 1.35 (3H, d, J 6.4 Hz), 1.24 (3H, d, J 6.4 Hz) and 1.16 (3H, d, J 7.2 Hz) ppm. Mass spectrum: FAB (thiodiethanol/Na matrix) observed mass MNa$^+$ 976. Calculated mass for $C_{48}H_{75}NO_{18}$, 953.5.

EXAMPLE 3

14-(S)-Hydroxy-13-O-methylamphotericin B methyl ester (E3)

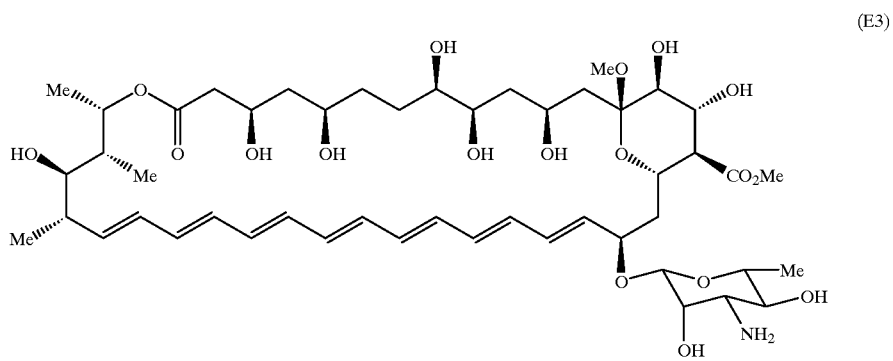

(E3)

To a solution of N-(9-fluorenylmethoxycarbonyl)-14-(S)-hydroxy-13-O-methyl amphotericin B methyl ester (D13) (63 mg, 0.053 mmol) in dimethylsulphoxide/methanol (0.6 ml:0.2 ml) under nitrogen was added piperidine (16 µl, 0.16 mmol). After stirring for 0.75 hours the reaction was poured into diethyl ether (400 ml). The precipitate was filtered and washed with diethyl ether and dried.

UV λmax (methanol) 406, 382.5, 363.5 and 346 nm. IR νmax (KBr disc) 3400, 2930, 1725, 1635, 1600, 1440, 1375, 1315, 1270, 1065, 1010, 890 and 850cm$^{-1}$. δH (400 MHz) [d$_5$ pyridine/d$_4$ methanol 1:1] 6.54–6.31 (12H, complex), 6.07 (1H, dd, J 14.6 and 6.4 Hz), 5.65 (1H, dd, J 14.5 and 9.4 Hz), 5.40 (1H, multiplet), 4.83 (1H, multiplet), 4.72 (1H, d, J 0.8 Hz), 4.50 (1H, dd, J 10.5 and 9.2 Hz), 4.44 (1H, complex), 4.32 (1H, multiplet), 4.26 (1H, multiplet), 4.15 (1H, d, J 3.0 Hz), 3.97 (1H, complex), 3.80–3.75 (4H, complex including a singlet at 3.77), 3.61 (1H, d, J 9.2 Hz), 3.52–3.44 (4H, complex), 3.32 (3H, s), 2.87–2.80 (2H, complex including dd at 2.85, J 9.2 and 3.1 Hz and triplet at 2.83, J 10.8 Hz), 2.57–2.49 (2H, complex including a dd at 2.52, J 16.6 and 8.6 Hz), 2.40 (1H, dd, J 16.6 and 3.7 Hz), 2.28 (1H, d J 14.7 Hz), 2.17 (1H, complex), 2.06–1.96 (3H, complex), 1.92–1.84 (2H, complex), 1.76–1.59 (6H, complex), 1.44 (3H, d, J 5.8 Hz), 1.33 (3H, d, J 6.4 Hz), 1.24 (3H, d, J 6.6 Hz) and 1.14 (3H, d, J 7.1 Hz) ppm. Mass spectrum: FAB (thiodiethanol/Na matrix) observed mass MNa$^+$ 990. Calculated mass for $C_{49}H_{77}NO_{18}$, 967.5.

EXAMPLE 4

14-(R)-Hydroxy-13-O-methylamphotericin B methyl ester (E4)

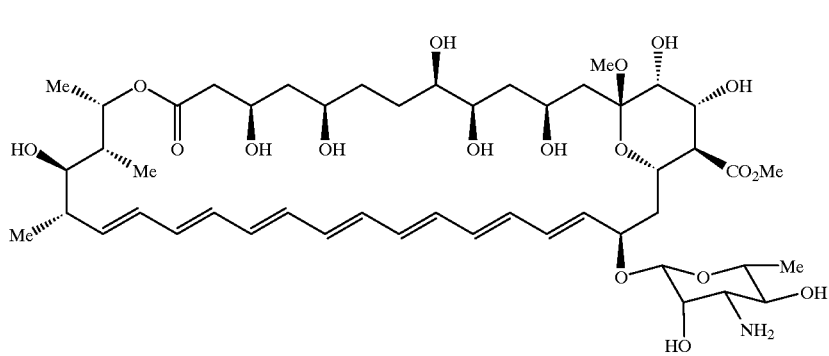

(E4)

The title compound was prepared from the compound of Description 15 using an analogous procedure to that described in Example 3.

Mass Spectrum: FAB (thiodiethanol/Na matrix); Observed mass, MNa+ 990. Calculated mass for $C_{49}H_{77}NO_{18}$, 967.5.

EXAMPLE 5

14-(R)-Hydroxyamphotericin B, allyl ester (E5)

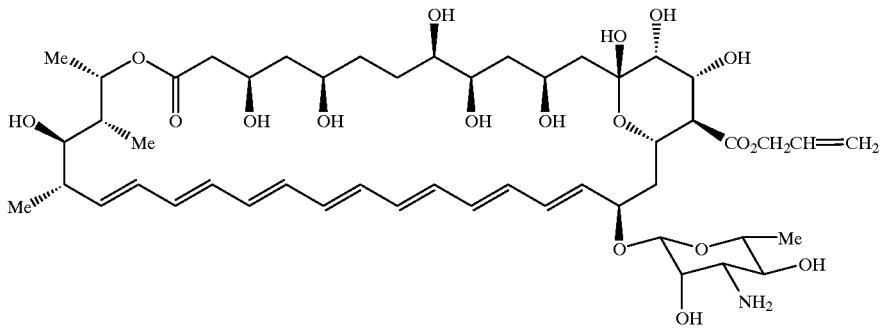

N-(9-Fluorenylmethoxycarbonyl)-14-(R)-hydroxyamphotericin B, allyl ester (D19) (0.82 g, 0.68 mmol) in dimethylsulphoxide (10 ml): methanol (3 ml) was treated at room temperature with piperidine (0.134 ml, 1.36 mmol). After 90 mins, methanol (7 ml) was added and the mixture poured into ether (21). The precipitate was filtered and washed with ether. Drying under vacuum gave the title product (E5) (0.60 g).

λmax (MeOH) 405 (ε147,000), 382 (129,000), 363 (82,000)nm. vmax (nujol) 3400, 1720cm$^{-1}$. $\delta^1$H (400 Mz) (CD$_3$OD: C$_5$D$_5$N; 1:1). Characteristic peaks include 1.16 (3H,d, J7.1 Hz), 1.24 (3H,d, J6.4 Hz), 1.35 (3H,d, J6.4 Hz), 1.44 (3H,d, J5.4 Hz), 2.48 (1H,dd, J16.9, 9.65 Hz), 2.82 (1H,dd, J9.3, 3.1 Hz), 3.14 (1H,t, J10.8 Hz), 3.85 (1H,d, J3.0 Hz), 3.94 (1H,m), 4.17 (1H,d, J3.1 Hz), 4.43 (1H,m), 5.25 (1H,m), 5.49 (2H,m), 5.61 (1H,m), 6.02 (1H,m).$\delta^{13}$C (68 MHz) (CD$_3$OD: C$_5$D$_5$N; 1:1) 12.63, 17.35, 18.39, 19.14, 31.55, 36.38, 38.38, 41.02, 41.24, 42.82, 43.24, 44.00, 44.87, 52.01, 57.9, 65.79, 66.65, 68.69, 69.46, 70.31, 70.48, 72.31, 72.80, 74.83, 75.07, 75.26, 76.39, 76.73, 79.07, 98.99, 100.43, 118.28, 130.49–134.89(m), 137.38, 137.56, 172.34, 174.26. Mass Spectrum (FAB: TDE-Na matrix). Found: MNa+, 1002. $C_{50}H_{77}O_{18}N$ requires M, 979.5.

EXAMPLE 6

14-(R)-Hydroxyamphotericin B (E6)

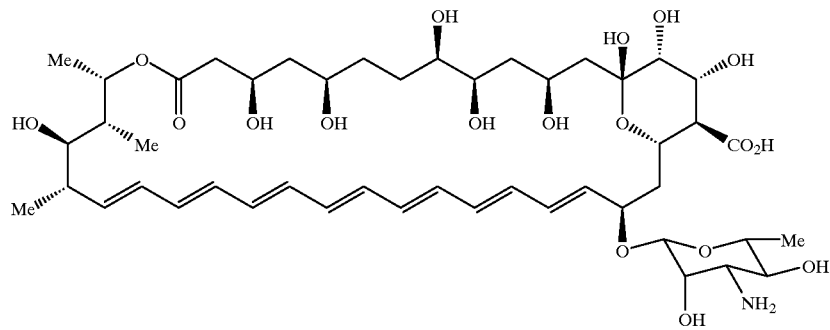

14-(R)-Hydroxyamphotericin B, allyl ester (E5) (0.11 g, 0.11 mmol) was added to tetrahydrofuran (6 ml) and methanol (0.5 ml) and insoluble residues filtered off. To the remaining solution, in the dark under nitrogen, was added pyrrolidine (40 μl, 0.47 mmol) and tetrakis (triphenylphosphine) palladium (0) (13 mg, 0.013 mmol). After 1 hour, the precipitate was collected by centrifugation. Washing of this solid sequentially in the tetrahydrofuran (40 ml) and acetone (40 ml) gave, after drying under vacuum, the title product (E6) (42 mg).

λmax (MeOH) 406 (ε108,000), 383 (100,000), 364 (65,000)nm. νmax (nujol) 3500–2400, 1710, 1570cm$^{-1}$. δ$^1$H (400 MHz) ((CD$_3$)$_2$SO). Characteristic signals include 0.92 (3H,d, J6.9 Hz), 1.04 (3H,d, J6.0 Hz), 1.11 (3H,d, J6.0 Hz), 5.22 (1H,m), 5.44 (1H,m). Mass Spectrum (FAB: TDE-Na matrix). Found: MNa$^+$, 962.5. $C_{47}H_{73}NO_{18}$ requires M, 939.5.

EXAMPLE 7

14-(S)-Hydroxyamphotericin B methyl ester-(L)-Aspartate (E7)

To a solution of (L)-aspartic acid (5.2 mg, 0.039 mmol) in distilled water (3 ml) was added portionwise 14-(S)-hydroxyamphotericin B methyl ester (E2) (37 mg, 0.039 mmol). After stirring for 0.5 hours the water was evaporated under vacuum to give the title salt (E7).

EXAMPLE 8

14-(R)-Hydroxyamphotericin B methyl ester (E8)

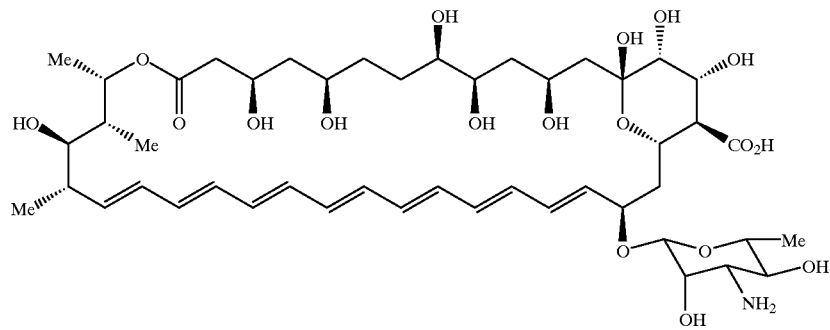

N-(9-Fluorenylmethoxycarbonyl)-14-(R)-hydroxyamphotericin B methyl ester (D20) (36.4 mg, 0.031 mmol) was dissolved in dimethylsulphoxide/methanol (3:1, 2 ml). Under nitrogen, piperidine (9 μl, 0.092 mmol) was added. After 2 hours the reaction was poured into diethyl ether (250 ml). The precipitate was centrifuged and washed with diethyl ether. Drying gave the title compound (E8).

UV λmax (methanol) 405, 382, 363 and 345 nm. IR νmax (KBr disc) 3415, 3007, 2924, 1717, 1633, 1438, 1384, 1324, 1289, 1196, 1175, 1094, 1069, 1011, 886 and 851cm$^{-1}$. δH (400) [d$_5$ pyridine/d$_4$ methanol 1:1] 6.66–6.28 (13H, complex), 5.63 (1H, multiplet), 5.50 (1H, dd, J 14.7 and 10.1 Hz), 4.86 (1H, multiplet), 4.75–4.67 (4H, complex), 4.45 (1H, multiplet), 4.26 (1H, multiplet), 3.96 (1H, multiplet), 3.88–3.86 (2H, complex including a doublet at 3.88, J 2.9 Hz), 3.76 (3H, s), 3.61 (1H, t, J 9.3 Hz), 3.50 (1H, multiplet), 3.42–3.36 (2H, complex), 3.14 (1H, t, J 10.8 Hz), 3.05 (1H, broad), 2.60–2.46 (3H, complex), 2.40–2.33 (2H, complex), 2.25 (1H, dd, J 4.6 and 14.9 Hz), 2.13–1.91 (5H, complex), 1.81–1.50 (5H, complex), 1.45 (3H, d, J 6.0 Hz), 1.36 (3H, d, J 6.4 Hz), 1.25 (3H, d, J 6.4 Hz) and 1.17 (3H, d, J 7.1 Hz) ppm. Mass spectrum: FAB (thiodiethanol/Na matrix) observed mass MNa$^+$ 977. Calculated mass for $C_{48}H_{75}NO_{18}$, 953.5.

EXAMPLE 9

16-Decarboxy-16-hydroxymethyl-14-(R)-hydroxyamphotericin B (E9)

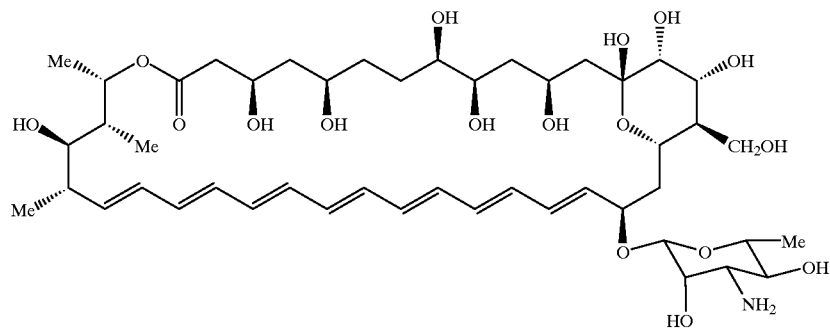

N-(9-Fluorenylmethoxycarbonyl)-16-decarboxy-16-hydroxymethylamphotericin B (D22) (108 mg, 0.09 mmol) was dissolved in dimethylsulphoxide/methanol (3:1, 2 ml). Under nitrogen, piperidine (14 µl, 0.15 mmol) was added and the reaction stirred for 2 hours. The solution was precipitated in diethyl ether, centrifuged and washed with ether. Drying have the title compound (E9).

UV λmax (methanol) 406, 382, 363 and 345 nm. IR vmax (KBr disc) 3391, 3013, 2964, 2930, 1716, 1631, 1448 and 1363cm$^{-1}$. δH (270 MHz) [d$_5$ pyridine:d$_4$ methanol 1:1] 6.70–6.30 (14H, complex), 5.65 (1H, multiplet), 4.94 (1H, s), 4.73 (3H, complex), 4.48 (2H, complex), 4.25 (1H, d), 4.18–3.87 (5H, complex), 3.67 (1H, complex), 3.59–3.35 (4H complex), 2.96 (1H, dd), 2.80–2.30 (5H, complex), 2.20–1.50 (11H, complex), 1.44 (3H, d, J 5.5 Hz), 1.36 (3H, d, J 6.3 Hz), 1.25 (3H, d, J 6.3 Hz) and 1.17 (3H, d, J 7.2 Hz) ppm. Mass spectrum : FAB (thiodiethanol/Na matrix) observed mass MNa$^+$ 948.5. Calculated mass for C$_{47}$H$_{75}$NO$_{17}$, 925.5.

What is claimed is:

1. A compound of formula (I), or a pharmaceutically acceptable salt thereof:

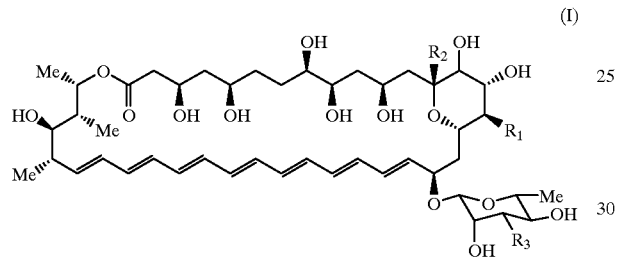

wherein R$_1$ is a carboxylic acid group, an ester thereof selected from the group consisting of alkoxycarbonyl, alkenyloxycarbonyl, aryloxycarbonyl, heteroaryloxycarbonyl, aralkyloxycarbonyl, and heteroaralkyloxycarbonyl, or a primary amide thereof, or —CHO, wherein any alkyl, alkenyl, or alkoxy group independently contains from one to six carbon atoms, wherein any aryl group is selected from the group consisting of phenyl and naphthyl either being unsubstituted or mono-, di-, or tri-substituted by a substituent selected from the group consisting of carboxy, C$_{1-6}$ alkoxycarbonyl, hydroxy-C$_{1-6}$ alkyl, C$_{1-6}$ alkoxy, halogen, and an amino optionally substituted by C$_{1-6}$ alkyl, and wherein any heteroaryl group is a 5- or 6-membered monocyclic or a 9- or 10-membered bicyclic group containing one or two heteroatoms independently selected from the group consisting of nitrogen, oxygen, and sulfur; R$_2$ is hydroxy, C$_{1-8}$ alkoxy or a fluorine atom; and R$_3$ is an amino group.

2. A compound according to claim 1 wherein R$_1$ is hydroxycarbonyl, C$_{1-4}$ alkoxycarbonyl, C$_{1-4}$ alkenyloxycarbonyl or hydroxymethyl.

3. A compound according to claim 1 wherein R$_1$ is methoxycarbonyl or prop-2-enyloxycarbonyl.

4. A compound according to claim 1 wherein R$_2$ is hydroxy, C$_{1-4}$ alkoxy or fluoro.

5. A compound according to claim 1 wherein R$_2$ is methoxy.

6. A compound according to claim 1 which exists in the 14(S)-stereoisomeric form.

7. A compound according to claim 1 which exists in the 14(R)-stereoisomeric form.

8. A compound selected from the group consisting of 13-dehydroxy-13-fluoro-14-(S)-hydroxyamphotericin B methyl ester, 14-(S)-hydroxyamphotericin B methyl ester, 14-(S)-hydroxy-13-O-methylamphotericin B methyl ester, 14-(R)-hydroxy-13-O-methylamphotericin B methyl ester, 14-(R)-hydroxyamphotericin B, allyl ester, 14-(R)-hydroxyamphotericin B, 14-(S)-hydroxyamphotericin B methyl ester-(L)-Aspartate, 14-(R)-hydroxyamphotericin B methyl ester and 16-decarboxy-16-hydroxymethyl-14-(R)-hydroxyamphotericin B.

9. An intermediate compound selected from the group consisting of:

N-(9-fluorenylmethoxycarbonyl)-13-O-(3-chlorobenzoyl)-14-(S)-hydroxy-3,5,8,9,11,15,35,2',4'-nona-O-triethyl-silylamphotericin B methyl ester, N-(9-fluorenylmethoxycarbonyl)-13-O-(3-chlorobenzoyl)-14-(S)-hydroxy-3,5,8,9,11,15,35,2',4'-nona-O-trimethyl-silyl amphotericin B methyl ester and N-(9-fluorenylmethoxycarbonyl)-13-O-(3-chlorobenzoyl)-14-(S)-hydroxy amphotericin B methyl ester.

10. A pharmaceutical composition comprising an antifungally effective amount of a compound of the formula (I), as defined in claim 1, or a pharmaceutically acceptable salt thereof, together with a pharmaceutically acceptable diluent or carrier.

11. A method of treatment of fungal infections in humans which comprises administering an effective anti-fungal amount of a compound of formula (I), as defined in claim 1 or a pharmaceutically acceptable salt thereof to a human in need of treatment for a fungal infection.

* * * * *